United States Patent [19]

Degen

[11] Patent Number: 5,606,029
[45] Date of Patent: Feb. 25, 1997

[54] GENE FOR A GROWTH FACTOR AND ITS CDNA AND PROTEIN

[75] Inventor: Sandra J. Degen, Cincinnati, Ohio

[73] Assignee: Children's Hospital Medical Center, Cincinnati, Ohio

[21] Appl. No.: 184,012

[22] Filed: Jan. 18, 1994

Related U.S. Application Data

[63] Continuation of Ser. No. 882,925, May 14, 1992, Pat. No. 5,315,000.

[51] Int. Cl.$^6$ .................... C07K 14/475; A61K 38/18; C12N 15/12
[52] U.S. Cl. ............................... 530/399; 536/23.5
[58] Field of Search ............... 530/399; 435/172.3, 435/69.4, 91, 320.1; 514/2.12; 424/69.4, 69.5; 536/23.5

[56] References Cited

U.S. PATENT DOCUMENTS 5,219,991   6/1993   Leonard et al. ............... 530/351

OTHER PUBLICATIONS

Skeel, Alison, *Macrophage Stimulating Protein: Purification, Partial Amino Acid Sequence, and Cellular Activity*, The Journal of Experimental Medicine, vol. 173, pp. 1227–1234.
Han et al. *Biochemistry* 30(40): 9768–80 (1991).
Degen et al. *Biochemistry* 30(40): 9781–91 (1991).
Naylor et al. *Nature* 329:451–54 (1987).
Harbour et al. *AntiCancer Res.* 10:23–28 (1990).
Naylor et al. *Genomics* 4:355–61 (1989).

*Primary Examiner*—John Ulm
*Assistant Examiner*—Christine Saoud
*Attorney, Agent, or Firm*—Wood, Herron & Evans, P.L.L.

[57] ABSTRACT

A growth factor protein similar in structure and function to hepatocyte growth factor has been discovered along with the DNA and cDNA coding for this in both the mouse and human. The DNA includes 18 exons and is homologous to DNA at the D3F15S2 locus on human chromosome 3; a region predicted to code for one or more tumor suppressor genes.

5 Claims, 1 Drawing Sheet

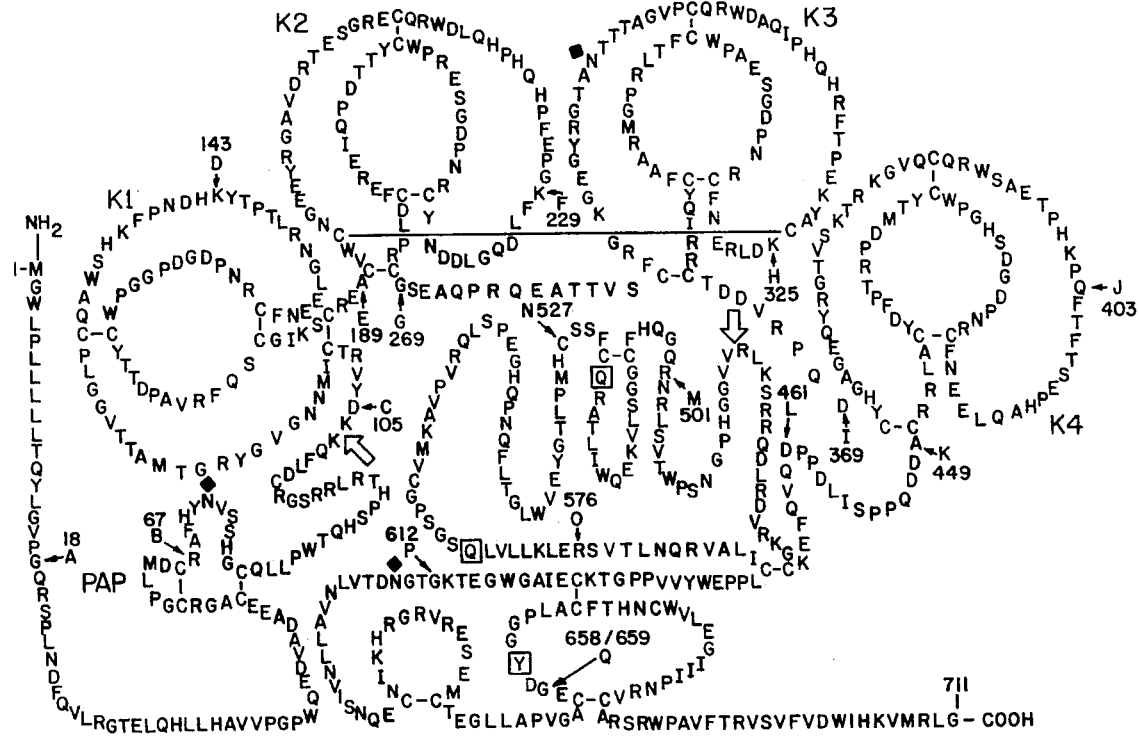

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 2219 base pairs
        ( B ) TYPE: nucleic acid
        ( C ) STRANDEDNESS: single
        ( D ) TOPOLOGY: linear ( i i ) MOLECULE TYPE: cDNA to mRNA ( i v ) ANTI-SENSE: no ( v i ) ORIGINAL SOURCE:
        ( A ) ORGANISM: human
        ( D ) DEVELOPMENTAL STAGE: fetal
        ( F ) TISSUE TYPE: liver ( v i i ) IMMEDIATE SOURCE:
        ( A ) LIBRARY: cDNA
        ( B ) CLONE: #33

( v i i i ) POSITION IN GENOME:
        ( A ) CHROMOSOME/SEGMENT: human 3p21/D3F15S2

( i x ) FEATURE:
        ( C ) IDENTIFICATION METHOD: experimental
        ( D ) OTHER INFORMATION: Includes five polymorphisms at the
            nucleotide level; one of which results in an amino acid
            substitution (nucleotide 619). Sequence ID NO:2:
            contains the identical sequence with the other polymorphic amino acid.

( x ) PUBLICATION INFORMATION:
( K ) RELEVANT RESIDUES IN SEQ ID NO: 1: FROM 1 TO 2219

( x i ) SEQUENCE DESCRIPTION: SEQ ID NO:1:

```
TC CTG CTG CTT CTG ACT CAA TAC TTA GGG GTC CCT GGG CAG CGC TCG        47
   Leu Leu Leu Leu Thr Gln Tyr Leu Gly Val Pro Gly Gln Arg Ser
             10                  15                  20

CCA TTG AAT GAC TTC CAA GTG CTC CGG GGC ACA GAG CTA CAG CAC CTG        95
Pro Leu Asn Asp Phe Gln Val Leu Arg Gly Thr Glu Leu Gln His Leu
             25                  30                  35

CTA CAT GCG GTG GTG CCC GGG CCT TGG CAG GAG GAT GTG GCA GAT GCT       143
Leu His Ala Val Val Pro Gly Pro Trp Gln Glu Asp Val Ala Asp Ala
             40                  45                  50

GAA GAG TGT GCT GGT CGC TGT GGG CCC TTA ATG GAC TGC CGG GCC TTC       191
Glu Glu Cys Ala Gly Arg Cys Gly Pro Leu Met Asp Cys Arg Ala Phe
         55                  60                  65

CAC TAC AAC GTG AGC AGC CAT GGT TGC CAA CTG CTG CCA TGG ACT CAA       239
His Tyr Asn Val Ser Ser His Gly Cys Gln Leu Leu Pro Trp Thr Gln
     70                  75                  80                  85

CAC TCG CCC CAC ACG AGG CTG CGG CGT TCT GGG CGC TGT GAC CTC TTC       287
His Ser Pro His Thr Arg Leu Arg Arg Ser Gly Arg Cys Asp Leu Phe
             90                  95                  100

CAG AAG AAA GAC TAC GTA CGG ACC TGC ATC ATG AAC AAT GGG GTT GGG       335
Gln Lys Lys Asp Tyr Val Arg Thr Cys Ile Met Asn Asn Gly Val Gly
             105                 110                 115

TAC CGG GGC ACC ATG GCC ACG ACC GTG GGT GGC CTG CCC TGC CAG GCT       383
Tyr Arg Gly Thr Met Ala Thr Thr Val Gly Gly Leu Pro Cys Gln Ala
             120                 125                 130

TGG AGC CAC AAG TTC CCG AAT GAT CAC AAG TAC ACG CCC ACT CTC CGG       431
Trp Ser His Lys Phe Pro Asn Asp His Lys Tyr Thr Pro Thr Leu Arg
     135                 140                 145

AAT GGC CTG GAA GAG AAC TTC TGC CGT AAC CCT GAT GGC GAC CCC GGA       479
Asn Gly Leu Glu Glu Asn Phe Cys Arg Asn Pro Asp Gly Asp Pro Gly
150                 155                 160                 165

GGT CCT TGG TGC TAC ACA ACA GAC CCT GCT GTG CGC TTC CAG AGC TGC       527
Gly Pro Trp Cys Tyr Thr Thr Asp Pro Ala Val Arg Phe Gln Ser Cys
             170                 175                 180

GGC ATC AAA TCC TGC CGG GAG GCC GCG TGT GTC TGG TGC AAT GGC GAG       575
Gly Ile Lys Ser Cys Arg Glu Ala Ala Cys Val Trp Cys Asn Gly Glu
             185                 190                 195

GAA TAC CGC GGC GCG GTA GAC CGC ACG GAG TCA GGG CGC GAG TGC CAG       623
Glu Tyr Arg Gly Ala Val Asp Arg Thr Glu Ser Gly Arg Glu Cys Gln
             200                 205                 210

CGC TGG GAT CTT CAG CAC CCG CAC CAG CAC CCC TTC GAG CCG GGC AAG       671
Arg Trp Asp Leu Gln His Pro His Gln His Pro Phe Glu Pro Gly Lys
     215                 220                 225

TTC CTC GAC CAA GGT CTG GAC GAC AAC TAT TGC CGG AAT CCT GAC GGC       719
Phe Leu Asp Gln Gly Leu Asp Asp Asn Tyr Cys Arg Asn Pro Asp Gly
230                 235                 240                 245

TCC GAG CGG CCA TGG TGC TAC ACT ACG GAT CCG CAG ATC GAG CGA GAG       767
Ser Glu Arg Pro Trp Cys Tyr Thr Thr Asp Pro Gln Ile Glu Arg Glu
             250                 255                 260

TTC TGT GAC CTC CCC CGC TGC GGG TCC GAG GCA CAG CCC CGC CAA GAG       815
Phe Cys Asp Leu Pro Arg Cys Gly Ser Glu Ala Gln Pro Arg Gln Glu
             265                 270                 275

GCC ACA ACT GTC AGC TGC TTC CGC GGG AAG GGT GAG GGC TAC CGG GGC       863
Ala Thr Thr Val Ser Cys Phe Arg Gly Lys Gly Glu Gly Tyr Arg Gly
             280                 285                 290

ACA GCC AAT ACC ACC ACT GCG GGC GTA CCT TGC CAG CGT TGG GAC GCG       911
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Thr | Ala | Asn | Thr | Thr | Thr | Ala | Gly | Val | Pro | Cys | Gln | Arg | Trp | Asp | Ala |      |
|     | 295 |     |     |     | 300 |     |     |     |     | 305 |     |     |     |     |     |      |
| CAA | ATC | CCT | CAT | CAG | CAC | CGA | TTT | ACG | CCA | GAA | AAA | TAC | GCG | TGC | AAA | 959  |
| Gln | Ile | Pro | His | Gln | His | Arg | Phe | Thr | Pro | Glu | Lys | Tyr | Ala | Cys | Lys |      |
| 310 |     |     |     |     | 315 |     |     |     |     | 320 |     |     |     |     | 325 |      |
| GAC | CTT | CGG | GAG | AAC | TTC | TGC | CGG | AAC | CCC | GAC | GGC | TCA | GAG | GCG | CCC | 1007 |
| Asp | Leu | Arg | Glu | Asn | Phe | Cys | Arg | Asn | Pro | Asp | Gly | Ser | Glu | Ala | Pro |      |
|     |     |     |     | 330 |     |     |     |     | 335 |     |     |     |     | 340 |     |      |
| TGG | TGC | TTC | ACA | CTG | CGG | CCC | GGC | ATG | CGC | GCG | GCC | TTT | TGC | TAC | CAG | 1055 |
| Trp | Cys | Phe | Thr | Leu | Arg | Pro | Gly | Met | Arg | Ala | Ala | Phe | Cys | Tyr | Gln |      |
|     |     |     | 345 |     |     |     |     | 350 |     |     |     |     | 355 |     |     |      |
| ATC | CGG | CGT | TGT | ACA | GAC | GAC | GTG | CGG | CCC | CAG | GAC | TGC | TAC | CAC | GGC | 1103 |
| Ile | Arg | Arg | Cys | Thr | Asp | Asp | Val | Arg | Pro | Gln | Asp | Cys | Tyr | His | Gly |      |
|     |     | 360 |     |     |     |     | 365 |     |     |     |     | 370 |     |     |     |      |
| GCA | GGG | GAG | CAG | TAC | CGC | GGC | ACG | GTC | AGC | AAG | ACC | CGC | AAG | GGT | GTC | 1151 |
| Ala | Gly | Glu | Gln | Tyr | Arg | Gly | Thr | Val | Ser | Lys | Thr | Arg | Lys | Gly | Val |      |
|     | 375 |     |     |     |     | 380 |     |     |     |     | 385 |     |     |     |     |      |
| CAG | TGC | CAG | CGC | TGG | TCC | GCT | GAG | ACG | CCG | CAC | AAG | CCG | CAG | TTC | ACG | 1199 |
| Gln | Cys | Gln | Arg | Trp | Ser | Ala | Glu | Thr | Pro | His | Lys | Pro | Gln | Phe | Thr |      |
| 390 |     |     |     |     | 395 |     |     |     |     | 400 |     |     |     |     | 405 |      |
| TTT | ACC | TCC | GAR | CCG | CAT | GCA | CAA | CTG | GAG | GAG | AAC | TTC | TGC | CGG | AAC | 1247 |
| Phe | Thr | Ser | Glu | Pro | His | Ala | Gln | Leu | Glu | Glu | Asn | Phe | Cys | Arg | Asn |      |
|     |     |     |     | 410 |     |     |     |     | 415 |     |     |     |     | 420 |     |      |
| CCA | GAT | GGG | GAT | AGC | CAT | GGG | CCC | TGG | TGC | TAC | ACG | ATG | GAC | CCA | AGG | 1295 |
| Pro | Asp | Gly | Asp | Ser | His | Gly | Pro | Trp | Cys | Tyr | Thr | Met | Asp | Pro | Arg |      |
|     |     |     | 425 |     |     |     |     | 430 |     |     |     |     | 435 |     |     |      |
| ACC | CCA | TTC | GAC | TAC | TGT | GCC | CTG | CGA | CGC | TGC | GCT | GAT | GAC | CAG | CCG | 1343 |
| Thr | Pro | Phe | Asp | Tyr | Cys | Ala | Leu | Arg | Arg | Cys | Ala | Asp | Asp | Gln | Pro |      |
|     |     | 440 |     |     |     |     | 445 |     |     |     |     | 450 |     |     |     |      |
| CCA | TCA | ATC | CTG | GAC | CCC | CCA | GAC | CAG | GTG | CAG | TTT | GAG | AAG | TGT | GGC | 1391 |
| Pro | Ser | Ile | Leu | Asp | Pro | Pro | Asp | Gln | Val | Gln | Phe | Glu | Lys | Cys | Gly |      |
|     | 455 |     |     |     |     | 460 |     |     |     |     | 465 |     |     |     |     |      |
| AAG | AGG | GTG | GAT | CGG | CTG | GAT | CAG | CGG | CGT | TCC | AAG | CTG | CGC | GTG | GTT | 1439 |
| Lys | Arg | Val | Asp | Arg | Leu | Asp | Gln | Arg | Arg | Ser | Lys | Leu | Arg | Val | Val |      |
| 470 |     |     |     |     | 475 |     |     |     |     | 480 |     |     |     |     | 485 |      |
| GGG | GGC | CAT | CCG | GGC | AAC | TCA | CCC | TGG | ACA | GTC | AGC | TTG | CGG | AAT | CGG | 1487 |
| Gly | Gly | His | Pro | Gly | Asn | Ser | Pro | Trp | Thr | Val | Ser | Leu | Arg | Asn | Arg |      |
|     |     |     |     | 490 |     |     |     |     | 495 |     |     |     |     | 500 |     |      |
| CAG | GGC | CAG | CAT | TTC | TGC | GGG | GGT | TCT | CTA | GTG | AAG | GAG | CAG | TGG | ATA | 1535 |
| Gln | Gly | Gln | His | Phe | Cys | Gly | Gly | Ser | Leu | Val | Lys | Glu | Gln | Trp | Ile |      |
|     |     |     |     | 505 |     |     |     |     | 510 |     |     |     |     | 515 |     |      |
| CTG | ACT | GCC | CGG | CAG | TGC | TTC | TCC | TCC | TGC | CAT | ATG | CCT | CTC | ACG | GGC | 1583 |
| Leu | Thr | Ala | Arg | Gln | Cys | Phe | Ser | Ser | Cys | His | Met | Pro | Leu | Thr | Gly |      |
|     |     | 520 |     |     |     |     | 525 |     |     |     |     | 530 |     |     |     |      |
| TAT | GAG | GTA | TGG | TTG | GGC | ACC | CTG | TTC | CAG | AAC | CCA | CAG | CAT | GGA | GAG | 1631 |
| Tyr | Glu | Val | Trp | Leu | Gly | Thr | Leu | Phe | Gln | Asn | Pro | Gln | His | Gly | Glu |      |
|     | 535 |     |     |     |     | 540 |     |     |     |     | 545 |     |     |     |     |      |
| CCA | AGC | CTA | CAG | CGG | GTC | CCA | GTA | GCC | AAG | ATG | GTG | TGT | GGG | CCC | TCA | 1679 |
| Pro | Ser | Leu | Gln | Arg | Val | Pro | Val | Ala | Lys | Met | Val | Cys | Gly | Pro | Ser |      |
| 550 |     |     |     |     | 555 |     |     |     |     | 560 |     |     |     |     | 565 |      |
| GGC | TCC | CAG | CTT | GTC | CTG | CTC | AAG | CTG | GAG | AGA | TCT | GTG | ACC | CTG | AAC | 1727 |
| Gly | Ser | Gln | Leu | Val | Leu | Leu | Lys | Leu | Glu | Arg | Ser | Val | Thr | Leu | Asn |      |
|     |     |     |     | 570 |     |     |     |     | 575 |     |     |     |     | 580 |     |      |
| CAG | CGY | GTG | GCC | CTG | ATC | TGC | CTG | CCC | CCT | GAA | TGG | TAT | GTG | GTG | CCT | 1775 |
| Gln | Arg | Val | Ala | Leu | Ile | Cys | Leu | Pro | Pro | Glu | Trp | Tyr | Val | Val | Pro |      |
|     |     |     | 585 |     |     |     |     | 590 |     |     |     |     | 595 |     |     |      |
| CCA | GGG | ACC | AAG | TGT | GAG | ATT | GCA | GGC | TGG | GGT | GAG | ACC | AAA | GGT | ACG | 1823 |
| Pro | Gly | Thr | Lys | Cys | Glu | Ile | Ala | Gly | Trp | Gly | Glu | Thr | Lys | Gly | Thr |      |
|     |     | 600 |     |     |     |     | 605 |     |     |     |     | 610 |     |     |     |      |
| GGT | AAT | GAC | ACA | GTC | CTA | AAT | GTG | GCC | TTG | CTG | AAT | GTC | ATC | TCC | AAC | 1871 |

```
Gly  Asn  Asp  Thr  Val  Leu  Asn  Val  Ala  Leu  Leu  Asn  Val  Ile  Ser  Asn
     615                      620                      625

CAG  GAG  TGT  AAC  ATC  AAR  CAC  CGA  GGA  CGT  GTG  CGK  GAG  AGT  GAG  ATG         1919
Gln  Glu  Cys  Asn  Ile  Lys  His  Arg  Gly  Arg  Val  Arg  Glu  Ser  Glu  Met
630                      635                      640                      645

TGC  ACT  GAG  GGA  CTG  TTG  GCC  CCT  GTG  GGG  GCC  TGT  GAG  GGT  GAC  TAC         1967
Cys  Thr  Glu  Gly  Leu  Leu  Ala  Pro  Val  Gly  Ala  Cys  Glu  Gly  Asp  Tyr
                    650                      655                      660

GGG  GGC  CCA  CTT  GCC  TGC  TTT  ACC  CAC  AAC  TGC  TGG  GTC  CTG  GAA  GGA         2015
Gly  Gly  Pro  Leu  Ala  Cys  Phe  Thr  His  Asn  Cys  Trp  Val  Leu  Glu  Gly
               665                      670                      675

ATT  ATA  ATC  CCC  AAC  CGA  GTA  TGC  GCA  AGG  TCC  CGC  TGG  CCA  GCT  GTC         2063
Ile  Ile  Ile  Pro  Asn  Arg  Val  Cys  Ala  Arg  Ser  Arg  Trp  Pro  Ala  Val
          680                      685                      690

TTC  ACG  CGT  GTC  TCT  GTG  TTT  GTG  GAC  TGG  ATT  CAC  AAG  GTC  ATG  AGA         2111
Phe  Thr  Arg  Val  Ser  Val  Phe  Val  Asp  Trp  Ile  His  Lys  Val  Met  Arg
     695                      700                      705

CTG  GGT  TAGGCCCAGC  CTTGATGCCA  TATGCCTTGG  GGAGGACAAA  ACTTCTTGTC                   2167
Leu  Gly
710

AGACATAAAG  CCATGTTTCC  TCTTTATGCC  TGTAAAAAAA  AAAAAAAAA  AA                          2219
```

( 2 ) INFORMATION FOR SEQ ID NO:2:

( i ) SEQUENCE CHARACTERISTICS:
        ( A ) LENGTH: 2219 base pairs
        ( B ) TYPE: nucleic acid
        ( C ) STRANDEDNESS: single
        ( D ) TOPOLOGY: linear ( i i ) MOLECULE TYPE: cDNA to mRNA ( i v ) ANTI-SENSE: no ( v i ) ORIGINAL SOURCE:
        ( A ) ORGANISM: human
        ( D ) DEVELOPMENTAL STAGE: fetal
        ( F ) TISSUE TYPE: liver ( v i i ) IMMEDIATE SOURCE:
        ( A ) LIBRARY: cDNA
        ( B ) CLONE: #33

( v i i i ) POSITION IN GENOME:
        ( A ) CHROMOSOME/SEGMENT: human 3p21/D3F15S2

( i x ) FEATURE:
        ( C ) IDENTIFICATION METHOD: experimental
        ( D ) OTHER INFORMATION: Includes five polymorphisms at the
            nucleotide level; one of which results in an amino acid
            substitution (nucleotide 619). Sequence ID NO:1:
            contains the identical sequence with the other
            polymorphic amino acid.

( x ) PUBLICATION INFORMATION:
        ( K ) RELEVANT RESIDUES IN SEQ ID NO: 2: FROM 1 TO 2219

( x i ) SEQUENCE DESCRIPTION: SEQ ID NO:2:

```
TC  CTG  CTG  CTT  CTG  ACT  CAA  TAC  TTA  GGG  GTC  CCT  GGG  CAG  CGC  TCG          47
    Leu  Leu  Leu  Leu  Thr  Gln  Tyr  Leu  Gly  Val  Pro  Gly  Gln  Arg  Ser
                    10                       15                       20

CCA  TTG  AAT  GAC  TTC  CAA  GTG  CTC  CGG  GGC  ACA  GAG  CTA  CAG  CAC  CTG         95
Pro  Leu  Asn  Asp  Phe  Gln  Val  Leu  Arg  Gly  Thr  Glu  Leu  Gln  His  Leu
               25                       30                       35

CTA  CAT  GCG  GTG  GTG  CCC  GGG  CCT  TGG  CAG  GAG  GAT  GTG  GCA  GAT  GCT         143
Leu  His  Ala  Val  Val  Pro  Gly  Pro  Trp  Gln  Glu  Asp  Val  Ala  Asp  Ala
          40                       45                       50

GAA  GAG  TGT  GCT  GGT  CGC  TGT  GGG  CCC  TTA  ATG  GAC  TGC  CGG  GCC  TTC         191
```

-continued

| | | | | | | | | | | | | | | |
|---|---|---|---|---|---|---|---|---|---|---|---|---|---|---|
| Glu | Glu 55 | Cys | Ala | Gly | Arg 60 | Cys | Gly | Pro | Leu | Met 65 | Asp | Cys | Arg | Ala | Phe |

| CAC | TAC | AAC | GTG | AGC | AGC | CAT | GGT | TGC | CAA | CTG | CTG | CCA | TGG | ACT | CAA | 239 |
|---|---|---|---|---|---|---|---|---|---|---|---|---|---|---|---|---|
| His 70 | Tyr | Asn | Val | Ser | Ser 75 | His | Gly | Cys | Gln | Leu 80 | Leu | Pro | Trp | Thr | Gln 85 | |

| CAC | TCG | CCC | CAC | ACG | AGG | CTG | CGG | CGT | TCT | GGG | CGC | TGT | GAC | CTC | TTC | 287 |
| His | Ser | Pro | His | Thr 90 | Arg | Leu | Arg | Arg | Ser 95 | Gly | Arg | Cys | Asp | Leu 100 | Phe | |

| CAG | AAG | AAA | GAC | TAC | GTA | CGG | ACC | TGC | ATC | ATG | AAC | AAT | GGG | GTT | GGG | 335 |
| Gln | Lys | Lys | Asp 105 | Tyr | Val | Arg | Thr | Cys 110 | Ile | Met | Asn | Asn | Gly 115 | Val | Gly | |

| TAC | CGG | GGC | ACC | ATG | GCC | ACG | ACC | GTG | GGT | GGC | CTG | CCC | TGC | CAG | GCT | 383 |
| Tyr | Arg | Gly 120 | Thr | Met | Ala | Thr | Thr 125 | Val | Gly | Gly | Leu | Pro 130 | Cys | Gln | Ala | |

| TGG | AGC | CAC | AAG | TTC | CCG | AAT | GAT | CAC | AAG | TAC | ACG | CCC | ACT | CTC | CGG | 431 |
| Trp | Ser | His 135 | Lys | Phe | Pro | Asn | Asp 140 | His | Lys | Tyr | Thr | Pro 145 | Thr | Leu | Arg | |

| AAT | GGC | CTG | GAA | GAG | AAC | TTC | TGC | CGT | AAC | CCT | GAT | GGC | GAC | CCC | GGA | 479 |
| Asn 150 | Gly | Leu | Glu | Glu | Asn 155 | Phe | Cys | Arg | Asn | Pro 160 | Asp | Gly | Asp | Pro | Gly 165 | |

| GGT | CCT | TGG | TGC | TAC | ACA | ACA | GAC | CCT | GCT | GTG | CGC | TTC | CAG | AGC | TGC | 527 |
| Gly | Pro | Trp | Cys | Tyr 170 | Thr | Thr | Asp | Pro | Ala 175 | Val | Arg | Phe | Gln | Ser 180 | Cys | |

| GGC | ATC | AAA | TCC | TGC | CGG | GAG | GCC | GCG | TGT | GTC | TGG | TGC | AAT | GGC | GAG | 575 |
| Gly | Ile | Lys | Ser 185 | Cys | Arg | Glu | Ala | Ala 190 | Cys | Val | Trp | Cys | Asn 195 | Gly | Glu | |

| GAA | TAC | CGC | GGC | GCG | GTA | GAC | CGC | ACG | GAG | TCA | GGG | CGC | GAG | TTC | CAG | 623 |
| Glu | Tyr | Arg | Gly 200 | Ala | Val | Asp | Arg | Thr 205 | Glu | Ser | Gly | Arg | Glu 210 | Phe | Gln | |

| CGC | TGG | GAT | CTT | CAG | CAC | CCG | CAC | CAG | CAC | CCC | TTC | GAG | CCG | GGC | AAG | 671 |
| Arg | Trp 215 | Asp | Leu | Gln | His | Pro 220 | His | Gln | His | Pro | Phe 225 | Glu | Pro | Gly | Lys | |

| TTC | CTC | GAC | CAA | GGT | CTG | GAC | GAC | AAC | TAT | TGC | CGG | AAT | CCT | GAC | GGC | 719 |
| Phe | Leu | Asp | Gln 230 | Gly | Leu | Asp | Asp | Asn 235 | Tyr | Cys | Arg | Asn | Pro 240 | Asp | Gly 245 | |

| TCC | GAG | CGG | CCA | TGG | TGC | TAC | ACT | ACG | GAT | CCG | CAG | ATC | GAG | CGA | GAG | 767 |
| Ser | Glu | Arg | Pro | Trp 250 | Cys | Tyr | Thr | Thr | Asp 255 | Pro | Gln | Ile | Glu | Arg 260 | Glu | |

| TTC | TGT | GAC | CTC | CCC | CGC | TGC | GGG | TCC | GAG | GCA | CAG | CCC | CGC | CAA | GAG | 815 |
| Phe | Cys | Asp | Leu | Pro 265 | Arg | Cys | Gly | Ser | Glu 270 | Ala | Gln | Pro | Arg | Gln 275 | Glu | |

| GCC | ACA | ACT | GTC | AGC | TGC | TTC | CGC | GGG | AAG | GGT | GAG | GGC | TAC | CGG | GGC | 863 |
| Ala | Thr | Thr | Val 280 | Ser | Cys | Phe | Arg | Gly 285 | Lys | Gly | Glu | Gly | Tyr 290 | Arg | Gly | |

| ACA | GCC | AAT | ACC | ACC | ACT | GCG | GGC | GTA | CCT | TGC | CAG | CGT | TGG | GAC | GCG | 911 |
| Thr | Ala | Asn | Thr 295 | Thr | Thr | Ala | Gly | Val 300 | Pro | Cys | Gln | Arg | Trp 305 | Asp | Ala | |

| CAA | ATC | CCT | CAT | CAG | CAC | CGA | TTT | ACG | CCA | GAA | AAA | TAC | GCG | TGC | AAA | 959 |
| Gln | Ile 310 | Pro | His | Gln | His | Arg 315 | Phe | Thr | Pro | Glu | Lys 320 | Tyr | Ala | Cys | Lys 325 | |

| GAC | CTT | CGG | GAG | AAC | TTC | TGC | CGG | AAC | CCC | GAC | GGC | TCA | GAG | GCG | CCC | 1007 |
| Asp | Leu | Arg | Glu | Asn 330 | Phe | Cys | Arg | Asn | Pro 335 | Asp | Gly | Ser | Glu | Ala 340 | Pro | |

| TGG | TGC | TTC | ACA | CTG | CGG | CCC | GGC | ATG | CGC | GCG | GCC | TTT | TGC | TAC | CAG | 1055 |
| Trp | Cys | Phe | Thr | Leu 345 | Arg | Pro | Gly | Met | Arg 350 | Ala | Ala | Phe | Cys | Tyr 355 | Gln | |

| ATC | CGG | CGT | TGT | ACA | GAC | GAC | GTG | CGG | CCC | CAG | GAC | TGC | TAC | CAC | GGC | 1103 |
| Ile | Arg | Arg 360 | Cys | Thr | Asp | Asp | Val 365 | Arg | Pro | Gln | Asp | Cys 370 | Tyr | His | Gly | |

| GCA | GGG | GAG | CAG | TAC | CGC | GGC | ACG | GTC | AGC | AAG | ACC | CGC | AAG | GGT | GTC | 1151 |

| | |
|---|---|
| Ala Gly Glu Gln Tyr Arg Gly Thr Val Ser Lys Thr Arg Lys Gly Val<br>375 380 385 | |
| CAG TGC CAG CGC TGG TCC GCT GAG ACG CCG CAC AAG CCG CAG TTC ACG<br>Gln Cys Gln Arg Trp Ser Ala Glu Thr Pro His Lys Pro Gln Phe Thr<br>390 395 400 405 | 1199 |
| TTT ACC TCC GAR CCG CAT GCA CAA CTG GAG GAG AAC TTC TGC CGG AAC<br>Phe Thr Ser Glu Pro His Ala Gln Leu Glu Glu Asn Phe Cys Arg Asn<br>410 415 420 | 1247 |
| CCA GAT GGG GAT AGC CAT GGG CCC TGG TGC TAC ACG ATG GAC CCA AGG<br>Pro Asp Gly Asp Ser His Gly Pro Trp Cys Tyr Thr Met Asp Pro Arg<br>425 430 435 | 1295 |
| ACC CCA TTC GAC TAC TGT GCC CTG CGA CGC TGC GCT GAT GAC CAG CCG<br>Thr Pro Phe Asp Tyr Cys Ala Leu Arg Arg Cys Ala Asp Asp Gln Pro<br>440 445 450 | 1343 |
| CCA TCA ATC CTG GAC CCC CCA GAC CAG GTG CAG TTT GAG AAG TGT GGC<br>Pro Ser Ile Leu Asp Pro Pro Asp Gln Val Gln Phe Glu Lys Cys Gly<br>455 460 465 | 1391 |
| AAG AGG GTG GAT CGG CTG GAT CAG CGG CGT TCC AAG CTG CGC GTG GTT<br>Lys Arg Val Asp Arg Leu Asp Gln Arg Arg Ser Lys Leu Arg Val Val<br>470 475 480 485 | 1439 |
| GGG GGC CAT CCG GGC AAC TCA CCC TGG ACA GTC AGC TTG CGG AAT CGG<br>Gly Gly His Pro Gly Asn Ser Pro Trp Thr Val Ser Leu Arg Asn Arg<br>490 495 500 | 1487 |
| CAG GGC CAG CAT TTC TGC GGG GGG TCT CTA GTG AAG GAG CAG TGG ATA<br>Gln Gly Gln His Phe Cys Gly Gly Ser Leu Val Lys Glu Gln Trp Ile<br>505 510 515 | 1535 |
| CTG ACT GCC CGG CAG TGC TTC TCC TCC TGC CAT ATG CCT CTC ACG GGC<br>Leu Thr Ala Arg Gln Cys Phe Ser Ser Cys His Met Pro Leu Thr Gly<br>520 525 530 | 1583 |
| TAT GAG GTA TGG TTG GGC ACC CTG TTC CAG AAC CCA CAG CAT GGA GAG<br>Tyr Glu Val Trp Leu Gly Thr Leu Phe Gln Asn Pro Gln His Gly Glu<br>535 540 545 | 1631 |
| CCA AGC CTA CAG CGG GTC CCA GTA GCC AAG ATG GTG TGT GGG CCC TCA<br>Pro Ser Leu Gln Arg Val Pro Val Ala Lys Met Val Cys Gly Pro Ser<br>550 555 560 565 | 1679 |
| GGC TCC CAG CTT GTC CTG CTC AAG CTG GAG AGA TCT GTG ACC CTG AAC<br>Gly Ser Gln Leu Val Leu Leu Lys Leu Glu Arg Ser Val Thr Leu Asn<br>570 575 580 | 1727 |
| CAG CGY GTG GCC CTG ATC TGC CTG CCC CCT GAA TGG TAT GTG GTG CCT<br>Gln Arg Val Ala Leu Ile Cys Leu Pro Pro Glu Trp Tyr Val Val Pro<br>585 590 595 | 1775 |
| CCA GGG ACC AAG TGT GAG ATT GCA GGC TGG GGT GAG ACC AAA GGT ACG<br>Pro Gly Thr Lys Cys Glu Ile Ala Gly Trp Gly Glu Thr Lys Gly Thr<br>600 605 610 | 1823 |
| GGT AAT GAC ACA GTC CTA AAT GTG GCC TTG CTG AAT GTC ATC TCC AAC<br>Gly Asn Asp Thr Val Leu Asn Val Ala Leu Leu Asn Val Ile Ser Asn<br>615 620 625 | 1871 |
| CAG GAG TGT AAC ATC AAR CAC CGA GGA CGT GTG CGK GAG AGT GAG ATG<br>Gln Glu Cys Asn Ile Lys His Arg Gly Arg Val Arg Glu Ser Glu Met<br>630 635 640 645 | 1919 |
| TGC ACT GAG GGA CTG TTG GCC CCT GTG GGG GCC TGT GAG GGT GAC TAC<br>Cys Thr Glu Gly Leu Leu Ala Pro Val Gly Ala Cys Glu Gly Asp Tyr<br>650 655 660 | 1967 |
| GGG GGC CCA CTT GCC TGC TTT ACC CAC AAC TGC TGG GTC CTG GAA GGA<br>Gly Gly Pro Leu Ala Cys Phe Thr His Asn Cys Trp Val Leu Glu Gly<br>665 670 675 | 2015 |
| ATT ATA ATC CCC AAC CGA GTA TGC GCA AGG TCC CGC TGG CCA GCT GTC<br>Ile Ile Ile Pro Asn Arg Val Cys Ala Arg Ser Arg Trp Pro Ala Val<br>680 685 690 | 2063 |
| TTC ACG CGT GTC TCT GTG TTT GTG GAC TGG ATT CAC AAG GTC ATG AGA | 2111 |

-continued

```
Phe  Thr  Arg  Val  Ser  Val  Phe  Val  Asp  Trp  Ile  His  Lys  Val  Met  Arg
     695                 700                      705

CTG  GGT  TAGGCCCAGC  CTTGATGCCA  TATGCCTTGG  GGAGGACAAA  ACTTCTTGTC                2167
Leu  Gly
710

AGACATAAAG  CCATGTTTCC  TCTTTATGCC  TGTAAAAAAA  AAAAAAAAAA  AA                      2219
```

( 2 ) INFORMATION FOR SEQ ID NO:3:

( i ) SEQUENCE CHARACTERISTICS:
        ( A ) LENGTH: 2021 base pairs
        ( B ) TYPE: nucleic acid
        ( C ) STRANDEDNESS: single
        ( D ) TOPOLOGY: linear ( i i ) MOLECULE TYPE: cDNA to mRNA ( i v ) ANTI-SENSE: no ( v i ) ORIGINAL SOURCE:
        ( A ) ORGANISM: human
        ( D ) DEVELOPMENTAL STAGE: fetal
        ( F ) TISSUE TYPE: liver ( v i i ) IMMEDIATE SOURCE:
        ( A ) LIBRARY: cDNA
        ( B ) CLONE: #19

( v i i i ) POSITION IN GENOME:
        ( A ) CHROMOSOME/SEGMENT: human 3p21/D3F15S2

( i x ) FEATURE:
        ( C ) IDENTIFICATION METHOD: experimental
        ( D ) OTHER INFORMATION: This sequence is a variant where two
            regions were found to be deleted when compared to SEQ ID
            NO:1.

( x ) PUBLICATION INFORMATION:
        ( K ) RELEVANT RESIDUES IN SEQ ID NO:3: FROM 1 TO 2021

( x i ) SEQUENCE DESCRIPTION: SEQ ID NO:3:

```
A  TGC  TTA  GGG  GTC  CCT  GGG  CAG  CGC  TCG  CCA  TTG  AAT  GAC  TTC  CAA        46
   Cys  Leu  Gly  Val  Pro  Gly  Gln  Arg  Ser  Pro  Leu  Asn  Asp  Phe  Gln
             15                      20                      25

GTG  CTC  CGG  GGC  ACA  GAG  CTA  CAG  CAC  CTG  CTA  CAT  GCG  GTG  GTG  CCC      94
Val  Leu  Arg  Gly  Thr  Glu  Leu  Gln  His  Leu  Leu  His  Ala  Val  Val  Pro
               30                      35                      40

GGG  CCT  TGG  CAG  GAG  GAT  GTG  GCA  GAT  GCT  GAA  GAG  TGT  GCT  GGT  CGC      142
Gly  Pro  Trp  Gln  Glu  Asp  Val  Ala  Asp  Ala  Glu  Glu  Cys  Ala  Gly  Arg
          45                      50                      55

TGT  GGG  CCC  TTA  ATG  GAC  TGC  CGG  GCC  TTC  CAC  TAC  AAC  GTG  AGC  AGC      190
Cys  Gly  Pro  Leu  Met  Asp  Cys  Arg  Ala  Phe  His  Tyr  Asn  Val  Ser  Ser
60                      65                      70                      75

CAT  GGT  TGC  CAA  CTG  CTG  CCA  TGG  ACT  CAA  CAC  TCG  CCC  CAC  ACG  AGG      238
His  Gly  Cys  Gln  Leu  Leu  Pro  Trp  Thr  Gln  His  Ser  Pro  His  Thr  Arg
                    80                      85                      90

CTG  CGG  CGT  TCT  GGG  CGC  TGT  GAC  CTC  TTC  CAG  AAG  AAA  GAC  TAC  GTA      286
Leu  Arg  Arg  Ser  Gly  Arg  Cys  Asp  Leu  Phe  Gln  Lys  Lys  Asp  Tyr  Val
               95                      100                     105

CGG  ACC  TGC  ATC  ATG  AAC  AAT  GGG  GTT  GGG  TAC  CGG  GGC  ACC  ATG  GCC      334
Arg  Thr  Cys  Ile  Met  Asn  Asn  Gly  Val  Gly  Tyr  Arg  Gly  Thr  Met  Ala
               110                     115                     120

ACG  ACC  GTG  GGT  GGC  CTG  CCC  TGC  CAG  GCT  TGG  AGC  CAC  AAG  TTC  CCG      382
Thr  Thr  Val  Gly  Gly  Leu  Pro  Cys  Gln  Ala  Trp  Ser  His  Lys  Phe  Pro
          125                     130                     135

AAT  GAT  CAC  AAG  TAC  ACG  CCC  ACT  CTC  CGG  AAT  GGC  CTG  GAA  GAG  AAC      430
Asn  Asp  His  Lys  Tyr  Thr  Pro  Thr  Leu  Arg  Asn  Gly  Leu  Glu  Glu  Asn
140                     145                     150                     155
```

```
TTC  TGC  CGT  AAC  CCT  GAT  GGC  GAC  CCC  GGA  GGT  CCT  TGG  TGC  TAC  ACA       478
Phe  Cys  Arg  Asn  Pro  Asp  Gly  Asp  Pro  Gly  Gly  Pro  Trp  Cys  Tyr  Thr
               160                 165                           170

ACA  GAC  CCT  GCT  GTG  CGC  TTC  CAG  AGC  TGC  GGC  ATC  AAA  TCC  TGC  CGG       526
Thr  Asp  Pro  Ala  Val  Arg  Phe  Gln  Ser  Cys  Gly  Ile  Lys  Ser  Cys  Arg
               175                 180                           185

GAG  GCC  GCG  TGT  GTC  TGG  TGC  AAT  GGC  GAG  GAA  TAC  CGC  GGC  GCG  GTA       574
Glu  Ala  Ala  Cys  Val  Trp  Cys  Asn  Gly  Glu  Glu  Tyr  Arg  Gly  Ala  Val
               190                 195                           200

GAC  CGC  ACG  GAG  TCA  GGG  CGC  GAG  TGC  CAG  CGC  TGG  GAT  CTT  CAG  CAC       622
Asp  Arg  Thr  Glu  Ser  Gly  Arg  Glu  Cys  Gln  Arg  Trp  Asp  Leu  Gln  His
     205                      210                      215

CCG  CAC  CAG  CAC  CCC  TTC  GAG  CCG  GGC  AAG  TTC  CTC  GAC  CAA  GGT  CTG       670
Pro  His  Gln  His  Pro  Phe  Glu  Pro  Gly  Lys  Phe  Leu  Asp  Gln  Gly  Leu
220                      225                      230                      235

GAC  GAC  AAC  TAT  TGC  CGG  AAT  CCT  GAC  GGC  TCC  GAG  CGG  CCA  TGG  TGC       718
Asp  Asp  Asn  Tyr  Cys  Arg  Asn  Pro  Asp  Gly  Ser  Glu  Arg  Pro  Trp  Cys
                    240                 245                           250

TAC  ACT  ACG  GAT  CCG  CAG  ATC  GAG  CGA  GAG  TTC  TGT  GAC  CTC  CCC  CGC       766
Tyr  Thr  Thr  Asp  Pro  Gln  Ile  Glu  Arg  Glu  Phe  Cys  Asp  Leu  Pro  Arg
               255                 260                           265

TGC  GGG  TCC  GAG  GCA  CAG  CCC  CGC  CAA  GAG  GCC  ACA  ACT  GTC  AGC  TGC       814
Cys  Gly  Ser  Glu  Ala  Gln  Pro  Arg  Gln  Glu  Ala  Thr  Thr  Val  Ser  Cys
          270                      275                      280

TTC  CGC  GGG  AAG  GGT  GAG  GGC  TAC  CGG  GGC  ACA  GCC  AAT  ACC  ACC  ACT       862
Phe  Arg  Gly  Lys  Gly  Glu  Gly  Tyr  Arg  Gly  Thr  Ala  Asn  Thr  Thr  Thr
          285                      290                      295

GCG  GGC  GTA  CCT  TGC  CAG  CGT  TGG  GAC  GCG  CAA  ATC  CCT  CAT  CAG  CAC       910
Ala  Gly  Val  Pro  Cys  Gln  Arg  Trp  Asp  Ala  Gln  Ile  Pro  His  Gln  His
300                      305                      310                      315

CGA  TTT  ACG  CCA  GAA  AAA  TAC  GCG  TGC  AAA  GAC  CTT  CGG  GAG  AAC  TTC       958
Arg  Phe  Thr  Pro  Glu  Lys  Tyr  Ala  Cys  Lys  Asp  Leu  Arg  Glu  Asn  Phe
                    320                 325                           330

TGC  CGG  AAC  CCC  GAC  GGC  TCA  GAG  GCG  CCC  TGG  TGC  TTC  ACA  CTG  CGG      1006
Cys  Arg  Asn  Pro  Asp  Gly  Ser  Glu  Ala  Pro  Trp  Cys  Phe  Thr  Leu  Arg
               335                 340                           345

CCC  GGC  ATG  CGC  GCG  GCC  TTT  TGC  TAC  CAG  ATC  CGG  CGT  TGT  ACA  GAC      1054
Pro  Gly  Met  Arg  Ala  Ala  Phe  Cys  Tyr  Gln  Ile  Arg  Arg  Cys  Thr  Asp
          350                      355                      360

GAC  GTG  CGG  CCC  CAG  GAC  TGC  TAC  CAC  GGC  GCA  GGG  GAG  CAG  TAC  CGC      1102
Asp  Val  Arg  Pro  Gln  Asp  Cys  Tyr  His  Gly  Ala  Gly  Glu  Gln  Tyr  Arg
     365                      370                      375

GGC  ACG  GTC  AGC  AAG  ACC  CGC  AAG  GGT  GTC  CAG  TGC  CAG  CGC  TGG  TCC      1150
Gly  Thr  Val  Ser  Lys  Thr  Arg  Lys  Gly  Val  Gln  Cys  Gln  Arg  Trp  Ser
380                      385                      390                      395

GCT  GAG  ACG  CCG  CAC  AAG  CCG  CAG  TTC  ACG  TTT  ACC  TCC  GAA  CCG  CAT      1198
Ala  Glu  Thr  Pro  His  Lys  Pro  Gln  Phe  Thr  Phe  Thr  Ser  Glu  Pro  His
               400                 405                           410

GCA  CAA  CTG  GAG  GAG  AAC  TTC  TGC  CGG  AAC  CCA  GAT  GGG  GAT  AGC  CAT      1246
Ala  Gln  Leu  Glu  Glu  Asn  Phe  Cys  Arg  Asn  Pro  Asp  Gly  Asp  Ser  His
               415                 420                           425

GGG  CCC  TGG  TGC  TAC  ACG  ATG  GAC  CCA  AGG  ACC  CCA  TTC  GAC  TAC  TGT      1294
Gly  Pro  Trp  Cys  Tyr  Thr  Met  Asp  Pro  Arg  Thr  Pro  Phe  Asp  Tyr  Cys
          430                      435                      440

GCC  CTG  CGA  CGC  TGC  GCT  GAT  GAC  CAG  CCG  CCA  TCA  ATC  CTG  GAC  CCC      1342
Ala  Leu  Arg  Arg  Cys  Ala  Asp  Asp  Gln  Pro  Pro  Ser  Ile  Leu  Asp  Pro
          445                      450                      455

CCA  GGC  AGG  GCC  AGC  ATT  TCT  GCG  GGG  GGT  CTC  TAGTGAAGGA GCAGTGGATA         1395
Pro  Gly  Arg  Ala  Ser  Ile  Ser  Ala  Gly  Gly  Leu
460                      465                 470
```

```
CTGACTGCCC  GGCAGTGCTT  CTCCTCCTGA  ACCCACAGCA  TGGAGAGCCA  AGCCTACAGC    1455

GGGTCCCAGT  AGCCAAGATG  GTGTGTGGGC  CCTCAGGCTC  CCAGCTTGTC  CTGCTCAAGC    1515

TGGAGAGATC  TGTGACCCTG  AACCAGCGCG  TGGCCCTGAT  CTGCCTGCCC  CCTGAATGGT    1575

ATGTGGTGCC  TCCAGGGACC  AAGTGTGAGA  TTGCAGGCTG  GGTGAGACC   AAAGGTACGG    1635

GTAATGACAC  AGTCCTAAAT  GTGGCCTTGC  TGAATGTCAT  CTCCAACCAG  GAGTGTAACA    1695

TCAAGCACCG  AGGACGTGTG  CGTGAGAGTG  AGATGTGCAC  TGAGGGACTG  TTGGCCCCTG    1755

TGGGGGCCTG  TGAGGGTGAC  TACGGGGGCC  CACTTGCCTG  CTTTACCCAC  AACTGCTGGG    1815

TCCTGGAAGG  AATTATAATC  CCCAACCGAG  TATGCGCAAG  GTCCCGCTGG  CCAGCTGTCT    1875

TCACGCGTGT  CTCTGTGTTT  GTGGACTGGA  TTCACAAGGT  CATGAGACTG  GGTTAGGCCC    1935

AGCCTTGATG  CCATATGCCT  TGGGGAGGAC  AAAACTTCTT  GTCAGACATA  AAGCCATGTT    1995

TCCTCTTTAA  AAAAAAAAAA  AAAAAA                                            2021
```

( 2 ) INFORMATION FOR SEQ ID NO:4:

( i ) SEQUENCE CHARACTERISTICS:
        ( A ) LENGTH: 2188 base pairs
        ( B ) TYPE: nucleic acid
        ( C ) STRANDEDNESS: single
        ( D ) TOPOLOGY: linear ( i i ) MOLECULE TYPE: cDNA to mRNA ( i v ) ANTI-SENSE: no ( v i ) ORIGINAL SOURCE:
        ( A ) ORGANISM: mouse
        ( B ) STRAIN: C57BL/6
        ( D ) DEVELOPMENTAL STAGE: adult
        ( F ) TISSUE TYPE: liver ( v i i ) IMMEDIATE SOURCE:
        ( A ) LIBRARY: cDNA
        ( B ) CLONE: ML5-2

( v i i i ) POSITION IN GENOME:
        ( A ) CHROMOSOME/SEGMENT: mouse 9, Hgfl locus
        ( B ) MAP POSITION: Trf-Gnai-2-Hgfl- Cck ( i x ) FEATURE:
        ( C ) IDENTIFICATION METHOD: experimental ( x ) PUBLICATION INFORMATION:
        ( K ) RELEVANT RESIDUES IN SEQ ID NO: 4: 1 TO 2188

( x i ) SEQUENCE DESCRIPTION: SEQ ID NO:4:

```
G  GCT  CTT  GGG  CCG  CGC  TCA  CCA  CTG  AAT  GAC  TTC  CAG  CTG  TTC  CGG         46
   Ala  Leu  Gly  Pro  Arg  Ser  Pro  Leu  Asn  Asp  Phe  Gln  Leu  Phe  Arg
                       20                  25                       30

GGC  ACA  GAG  TTA  AGG  AAC  CTG  TTA  CAC  ACA  GCG  GTG  CCG  GGG  CCA  TGG        94
Gly  Thr  Glu  Leu  Arg  Asn  Leu  Leu  His  Thr  Ala  Val  Pro  Gly  Pro  Trp
                35                        40                       45

CAG  GAG  GAT  GTG  GCA  GAT  GCT  GAG  GAG  TGT  GCT  AGG  CGC  TGT  GGG  CCC       142
Gln  Glu  Asp  Val  Ala  Asp  Ala  Glu  Glu  Cys  Ala  Arg  Arg  Cys  Gly  Pro
               50                        55                       60

CTT  CTG  GAC  TGT  CGG  GCC  TTC  CAC  TAC  AAC  ATG  AGC  AGC  CAT  GGT  TGC       190
Leu  Leu  Asp  Cys  Arg  Ala  Phe  His  Tyr  Asn  Met  Ser  Ser  His  Gly  Cys
              65                        70                       75

CAG  CTG  CTG  CCG  TGG  ACC  CAG  CAC  TCG  CTG  CAC  ACA  CAG  CTA  TAC  CAC       238
Gln  Leu  Leu  Pro  Trp  Thr  Gln  His  Ser  Leu  His  Thr  Gln  Leu  Tyr  His
         80                        85                       90

TCG  AGT  CTG  TGC  CAT  CTC  TTC  CAG  AAG  AAA  GAT  TAT  GTG  CGG  ACC  TGC       286
Ser  Ser  Leu  Cys  His  Leu  Phe  Gln  Lys  Lys  Asp  Tyr  Val  Arg  Thr  Cys
```

|  | 95 |  |  |  | 100 |  |  |  |  | 105 |  |  |  |  | 110 |  |  |
|---|---|---|---|---|---|---|---|---|---|---|---|---|---|---|---|---|---|
| ATT | ATG | GAC | AAT | GGG | GTC | AGC | TAC | CGG | GGC | ACT | GTG | GCC | AGG | ACA | GCT | | 334 |
| Ile | Met | Asp | Asn | Gly | Val | Ser | Tyr | Arg | Gly | Thr | Val | Ala | Arg | Thr | Ala | | |
| | | | | 115 | | | | | 120 | | | | | 125 | | | |
| GGT | GGC | CTG | CCC | TGC | CAA | GCC | TGG | AGT | CGC | AGG | TTC | CCC | AAT | GAC | CAC | | 382 |
| Gly | Gly | Leu | Pro | Cys | Gln | Ala | Trp | Ser | Arg | Arg | Phe | Pro | Asn | Asp | His | | |
| | | | 130 | | | | | 135 | | | | | 140 | | | | |
| AAG | TAT | ACG | CCC | ACG | CCA | AAG | AAT | GGC | CTG | GAA | GAG | AAC | TTC | TGT | AGG | | 430 |
| Lys | Tyr | Thr | Pro | Thr | Pro | Lys | Asn | Gly | Leu | Glu | Glu | Asn | Phe | Cys | Arg | | |
| | | 145 | | | | | 150 | | | | | 155 | | | | | |
| AAC | CCT | GAT | GGG | GAT | CCC | AGA | GGT | CCC | TGG | TGC | TAC | ACA | ACA | AAC | CGC | | 478 |
| Asn | Pro | Asp | Gly | Asp | Pro | Arg | Gly | Pro | Trp | Cys | Tyr | Thr | Thr | Asn | Arg | | |
| | 160 | | | | | 165 | | | | | 170 | | | | | | |
| AGT | GTG | CGT | TTC | CAG | AGC | TGT | GGC | ATC | AAA | ACC | TGC | AGG | GAG | GCT | GTT | | 526 |
| Ser | Val | Arg | Phe | Gln | Ser | Cys | Gly | Ile | Lys | Thr | Cys | Arg | Glu | Ala | Val | | |
| 175 | | | | | 180 | | | | | 185 | | | | | 190 | | |
| TGT | GTT | CTG | TGC | AAC | GGT | GAG | GAT | TAC | CGT | GGC | GAG | GTA | GAC | GTT | ACA | | 574 |
| Cys | Val | Leu | Cys | Asn | Gly | Glu | Asp | Tyr | Arg | Gly | Glu | Val | Asp | Val | Thr | | |
| | | | | 195 | | | | | 200 | | | | | 205 | | | |
| GAG | TCA | GGG | CGG | GAG | TGT | CAA | CGC | TGG | GAC | CTG | CAG | CAC | CCC | CAC | TCG | | 622 |
| Glu | Ser | Gly | Arg | Glu | Cys | Gln | Arg | Trp | Asp | Leu | Gln | His | Pro | His | Ser | | |
| | | | 210 | | | | | 215 | | | | | 220 | | | | |
| CAC | CCT | TTC | CAG | CCT | GAA | AAG | TTC | CTA | GAC | AAA | GAT | CTG | AAA | GAC | AAC | | 670 |
| His | Pro | Phe | Gln | Pro | Glu | Lys | Phe | Leu | Asp | Lys | Asp | Leu | Lys | Asp | Asn | | |
| | | 225 | | | | | 230 | | | | | 235 | | | | | |
| TAT | TGT | CGT | AAT | CCG | GAC | GGA | TCT | GAG | CGG | CCC | TGG | TGC | TAC | ACC | ACA | | 718 |
| Tyr | Cys | Arg | Asn | Pro | Asp | Gly | Ser | Glu | Arg | Pro | Trp | Cys | Tyr | Thr | Thr | | |
| | 240 | | | | | 245 | | | | | 250 | | | | | | |
| GAC | CCG | AAT | GTT | GAG | CGA | GAA | TTC | TGC | GAC | CTG | CCC | AGT | TGC | GGG | CCT | | 766 |
| Asp | Pro | Asn | Val | Glu | Arg | Glu | Phe | Cys | Asp | Leu | Pro | Ser | Cys | Gly | Pro | | |
| 255 | | | | | 260 | | | | | 265 | | | | | 270 | | |
| AAC | CTG | CCT | CCG | ACC | GTC | AAA | GGA | TCC | AAG | TCA | CAG | CGG | CGC | AAC | AAG | | 814 |
| Asn | Leu | Pro | Pro | Thr | Val | Lys | Gly | Ser | Lys | Ser | Gln | Arg | Arg | Asn | Lys | | |
| | | | | 275 | | | | | 280 | | | | | 285 | | | |
| GGC | AAG | GCT | CTT | AAC | TGC | TTC | CGC | GGA | AAA | GGT | GAA | GAC | TAT | CGA | GGC | | 862 |
| Gly | Lys | Ala | Leu | Asn | Cys | Phe | Arg | Gly | Lys | Gly | Glu | Asp | Tyr | Arg | Gly | | |
| | | | 290 | | | | | 295 | | | | | 300 | | | | |
| ACA | ACC | AAT | ACC | ACC | TCT | GCG | GGC | GTG | CCC | TGC | CAG | CGG | TGG | GAT | GCG | | 910 |
| Thr | Thr | Asn | Thr | Thr | Ser | Ala | Gly | Val | Pro | Cys | Gln | Arg | Trp | Asp | Ala | | |
| | | 305 | | | | | 310 | | | | | 315 | | | | | |
| CAG | AGT | CCA | CAC | CAG | CAC | CGC | TTT | GTG | CCA | GAG | AAA | TAT | GCT | TGC | AAG | | 958 |
| Gln | Ser | Pro | His | Gln | His | Arg | Phe | Val | Pro | Glu | Lys | Tyr | Ala | Cys | Lys | | |
| | 320 | | | | | 325 | | | | | 330 | | | | | | |
| GAC | CTT | CGT | GAG | AAT | TTC | TGC | CGG | AAT | CCT | GAT | GGC | TCC | GAG | GCG | CCT | | 1006 |
| Asp | Leu | Arg | Glu | Asn | Phe | Cys | Arg | Asn | Pro | Asp | Gly | Ser | Glu | Ala | Pro | | |
| 335 | | | | | 340 | | | | | 345 | | | | | 350 | | |
| TGG | TGC | TTC | ACA | TCT | CGA | CCT | GGT | TTG | CGC | ATG | GCC | TTC | TGC | CAC | CAG | | 1054 |
| Trp | Cys | Phe | Thr | Ser | Arg | Pro | Gly | Leu | Arg | Met | Ala | Phe | Cys | His | Gln | | |
| | | | | 355 | | | | | 360 | | | | | 365 | | | |
| ATC | CCA | CGC | TGC | ACT | GAA | GAA | CTG | GTG | CCA | GAG | GGA | TGC | TAC | CAC | GGC | | 1102 |
| Ile | Pro | Arg | Cys | Thr | Glu | Glu | Leu | Val | Pro | Glu | Gly | Cys | Tyr | His | Gly | | |
| | | | 370 | | | | | 375 | | | | | 380 | | | | |
| TCA | GGT | GAA | CAG | TAT | CGT | GGC | TCA | GTC | AGC | AAG | ACG | CGC | AAG | GGC | GTT | | 1150 |
| Ser | Gly | Glu | Gln | Tyr | Arg | Gly | Ser | Val | Ser | Lys | Thr | Arg | Lys | Gly | Val | | |
| | | 385 | | | | | 390 | | | | | 395 | | | | | |
| CAG | TGC | CAG | CAC | TGG | TCC | TCT | GAG | ACA | CCG | CAC | AAG | CCA | CAA | TTT | ACA | | 1198 |
| Gln | Cys | Gln | His | Trp | Ser | Ser | Glu | Thr | Pro | His | Lys | Pro | Gln | Phe | Thr | | |
| | 400 | | | | | 405 | | | | | 410 | | | | | | |
| CCC | ACC | TCG | GCA | CCG | CAG | GCG | GGA | CTG | GAG | GCC | AAC | TTC | TGC | AGG | AAT | | 1246 |
| Pro | Thr | Ser | Ala | Pro | Gln | Ala | Gly | Leu | Glu | Ala | Asn | Phe | Cys | Arg | Asn | | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| 415 |     |     |     |     | 420 |     |     |     |     | 425 |     |     |     |     | 430 |      |
| CCT | GAT | GGG | GAT | AGC | CAT | GGG | CCC | TGG | TGC | TAT | ACC | TTG | GAC | CCG | GAT | 1294 |
| Pro | Asp | Gly | Asp | Ser | His | Gly | Pro | Trp | Cys | Tyr | Thr | Leu | Asp | Pro | Asp |      |
|     |     |     |     | 435 |     |     |     |     | 440 |     |     |     |     | 445 |     |      |
| ATC | CTG | TTT | GAC | TAC | TGT | GCC | CTA | CAG | CGC | TGT | GAT | GAT | GAC | CAG | CCA | 1342 |
| Ile | Leu | Phe | Asp | Tyr | Cys | Ala | Leu | Gln | Arg | Cys | Asp | Asp | Asp | Gln | Pro |      |
|     |     |     | 450 |     |     |     |     | 455 |     |     |     |     | 460 |     |     |      |
| CCA | TCC | ATT | CTG | GAC | CCC | CCA | GAC | CAG | GTG | GTG | TTT | GAA | AAG | TGT | GGC | 1390 |
| Pro | Ser | Ile | Leu | Asp | Pro | Pro | Asp | Gln | Val | Val | Phe | Glu | Lys | Cys | Gly |      |
|     |     | 465 |     |     |     |     | 470 |     |     |     |     | 475 |     |     |     |      |
| AAG | AGA | GTT | GAC | AAG | AGT | AAT | AAA | CTT | CGT | GTG | GTG | GGA | GGC | CAT | CCT | 1438 |
| Lys | Arg | Val | Asp | Lys | Ser | Asn | Lys | Leu | Arg | Val | Val | Gly | Gly | His | Pro |      |
|     | 480 |     |     |     |     | 485 |     |     |     |     | 490 |     |     |     |     |      |
| GGG | AAC | TCC | CCA | TGG | ACG | GTC | AGC | TTG | CGG | AAT | CGA | CAG | GGC | CAG | CAT | 1486 |
| Gly | Asn | Ser | Pro | Trp | Thr | Val | Ser | Leu | Arg | Asn | Arg | Gln | Gly | Gln | His |      |
| 495 |     |     |     |     | 500 |     |     |     |     | 505 |     |     |     |     | 510 |      |
| TTC | TGT | GGG | GGC | TCC | CTA | GTG | AAG | GAG | CAG | TGG | GTA | CTG | ACT | GCC | CGG | 1534 |
| Phe | Cys | Gly | Gly | Ser | Leu | Val | Lys | Glu | Gln | Trp | Val | Leu | Thr | Ala | Arg |      |
|     |     |     |     | 515 |     |     |     |     | 520 |     |     |     |     | 525 |     |      |
| CAA | TGC | ATC | TGG | TCA | TGC | CAC | GAA | CCT | CTC | ACA | GGA | TAC | GAG | GTA | TGG | 1582 |
| Gln | Cys | Ile | Trp | Ser | Cys | His | Glu | Pro | Leu | Thr | Gly | Tyr | Glu | Val | Trp |      |
|     |     |     | 530 |     |     |     |     | 535 |     |     |     |     | 540 |     |     |      |
| TTG | GGT | ACA | ATT | AAC | CAG | AAC | CCA | CAG | CCT | GGA | GAG | GCA | AAC | CTG | CAG | 1630 |
| Leu | Gly | Thr | Ile | Asn | Gln | Asn | Pro | Gln | Pro | Gly | Glu | Ala | Asn | Leu | Gln |      |
|     |     | 545 |     |     |     |     | 550 |     |     |     |     | 555 |     |     |     |      |
| AGG | GTC | CCA | GTG | GCC | AAG | GCA | GTG | TGC | GGC | CCT | GCA | GGC | TCC | CAG | CTT | 1678 |
| Arg | Val | Pro | Val | Ala | Lys | Ala | Val | Cys | Gly | Pro | Ala | Gly | Ser | Gln | Leu |      |
|     | 560 |     |     |     |     | 565 |     |     |     |     | 570 |     |     |     |     |      |
| GTT | CTG | CTC | AAG | CTG | GAG | AGA | CCT | GTG | ATC | CTG | AAC | CAT | CAC | GTG | GCC | 1726 |
| Val | Leu | Leu | Lys | Leu | Glu | Arg | Pro | Val | Ile | Leu | Asn | His | His | Val | Ala |      |
| 575 |     |     |     |     | 580 |     |     |     |     | 585 |     |     |     |     | 590 |      |
| CTG | ATT | TGC | CTG | CCT | CCT | GAA | CAG | TAT | GTG | GTA | CCT | CCA | GGG | ACC | AAG | 1774 |
| Leu | Ile | Cys | Leu | Pro | Pro | Glu | Gln | Tyr | Val | Val | Pro | Pro | Gly | Thr | Lys |      |
|     |     |     |     | 595 |     |     |     |     | 600 |     |     |     |     | 605 |     |      |
| TGT | GAG | ATC | GCA | GGC | TGG | GGT | GAA | TCC | ATC | GGT | ACA | AGC | AAT | AAC | ACA | 1822 |
| Cys | Glu | Ile | Ala | Gly | Trp | Gly | Glu | Ser | Ile | Gly | Thr | Ser | Asn | Asn | Thr |      |
|     |     |     | 610 |     |     |     |     | 615 |     |     |     |     | 620 |     |     |      |
| GTC | CTT | CAT | GTG | GCC | TCG | ATG | AAT | GTC | ATC | TCC | AAC | CAG | GAA | TGT | AAC | 1870 |
| Val | Leu | His | Val | Ala | Ser | Met | Asn | Val | Ile | Ser | Asn | Gln | Glu | Cys | Asn |      |
|     |     | 625 |     |     |     |     | 630 |     |     |     |     | 635 |     |     |     |      |
| ACG | AAG | TAC | CGA | GGA | CAC | ATA | CAA | GAG | AGT | GAG | ATA | TGC | ACC | CAG | GGA | 1918 |
| Thr | Lys | Tyr | Arg | Gly | His | Ile | Gln | Glu | Ser | Glu | Ile | Cys | Thr | Gln | Gly |      |
|     | 640 |     |     |     |     | 645 |     |     |     |     | 650 |     |     |     |     |      |
| CTG | GTG | GTC | CCT | GTG | GGG | GCT | TGT | GAG | GGT | GAC | TAC | GGG | GGC | CCA | CTT | 1966 |
| Leu | Val | Val | Pro | Val | Gly | Ala | Cys | Glu | Gly | Asp | Tyr | Gly | Gly | Pro | Leu |      |
| 655 |     |     |     |     | 660 |     |     |     |     | 665 |     |     |     |     | 670 |      |
| GCC | TGC | TAT | ACC | CAT | GAC | TGC | TGG | GTC | CTA | CAG | GGA | CTT | ATC | ATC | CCG | 2014 |
| Ala | Cys | Tyr | Thr | His | Asp | Cys | Trp | Val | Leu | Gln | Gly | Leu | Ile | Ile | Pro |      |
|     |     |     |     | 675 |     |     |     |     | 680 |     |     |     |     | 685 |     |      |
| AAC | AGA | GTG | TGT | GCA | CGG | CCC | CGC | TGG | CCA | GCT | ATC | TTC | ACA | CGG | GTG | 2062 |
| Asn | Arg | Val | Cys | Ala | Arg | Pro | Arg | Trp | Pro | Ala | Ile | Phe | Thr | Arg | Val |      |
|     |     |     | 690 |     |     |     |     | 695 |     |     |     |     | 700 |     |     |      |
| TCT | GTG | TTC | GTG | GAC | TGG | ATT | AAC | AAG | GTC | ATG | CAG | CTG | GAG |     |     | 2104 |
| Ser | Val | Phe | Val | Asp | Trp | Ile | Asn | Lys | Val | Met | Gln | Leu | Glu |     |     |      |
|     |     | 705 |     |     |     |     | 710 |     |     |     |     | 715 |     |     |     |      |

TAGGCCTGCT TTTGAGCCCT TAGAGATGTC AAGACTTCTC AAACATAAAG CGGCCTTTTC     2164

TCTCTGTCAA AAAAAAAAAA AAAA     2188

( 2 ) INFORMATION FOR SEQ ID NO:5:

( i ) SEQUENCE CHARACTERISTICS:
    ( A ) LENGTH: 6751 base pairs
    ( B ) TYPE: nucleic acid
    ( C ) STRANDEDNESS: single
    ( D ) TOPOLOGY: linear ( i i ) MOLECULE TYPE: genomic DNA ( i v ) ANTI-SENSE: no ( v i ) ORIGINAL SOURCE:
    ( A ) ORGANISM: mouse
    ( B ) STRAIN: Balb/c
    ( D ) DEVELOPMENTAL STAGE: adult
    ( F ) TISSUE TYPE: liver ( v i i ) IMMEDIATE SOURCE:
    ( A ) LIBRARY: genomic
    ( B ) CLONE: MGL5-12

( v i i i ) POSITION IN GENOME:
    ( A ) CHROMOSOME/SEGMENT: mouse 9, Hgfl locus
    ( B ) MAP POSITION: Trf-Gnai-2-Hgfl- Cck ( i x ) FEATURE:
    ( C ) IDENTIFICATION METHOD: experimental ( x ) PUBLICATION INFORMATION:
    ( K ) RELEVANT RESIDUES IN SEQ ID NO: 5: 1 TO 6751

( x i ) SEQUENCE DESCRIPTION: SEQ ID NO:5:

```
AGATCTGATC  GGCCAGGGGC  TCGAGGGGAG  TCACCGAACC  CGCCCGGCTC  ATAGCCAGGC       60

CGCCTCTCAC  TCACCCCCGG  CCTCAGCCTC  CGCGACCGGC  TCACAACATC  CGCCCAGCTT      120

TTCGGCTACG  GCACCCGTCC  AGGCCAAACC  GCGTGCTCGC  TCGAGCGCTG  CTCCAGCCGC      180

GCACGCGCAT  ATGCACAGAC  CGCAACAGGC  TGGCAGAAAA  CCCTCCTCCG  TCTCCTACCA      240

AGGTGTTTAC  CCGTTTTGCC  TGATGGTCCA  CCTGTTTCGC  CCCCACCTTT  CCTAGCCCAG      300

CCGTAGCAGG  GACTATGTTC  TAATCGGTCC  CTAGGTCCAC  CTGTCTTAAC  TCCTACCTTG      360

CCTGGAGGAG  GCCTGACCCA  CATGCAGCCT  GAAAGACCAC  TTCTGACAGC  AGATTTGCTA      420

CCTGTCACAG  CCGCGCACGC  CCCCTCCAGA  TGGTCATTGA  CACCAGATCC  AATGGGCAGG      480

GTTGCTTAGC  TTACCCTGGT  TTGACACTTC  TGAGGGGCGA  TGGGATGGAT  GCTCCTCGGA      540

TGTGCTGCTA  GGGGTGTAGG  CTGACTGCCC  TACAGCTGGG  ACTCAGCTGA  TAAGGCAGCT      600

TGAACAGGGA  GAGGCAGCAT  TGGGACTGGG  GAAATTGCAG  TCCTCACTTT  ACAAGAAGAA      660

ACTGAGGCCC  AGAAAAGTAT  AATCCAGGGG  TCTGGGAAAT  CTTGGCAACT  CCTGTATAGC      720

AGAGTCTTTT  GGCATAGAAG  TGTCAGTGGT  GATGGCAGCC  ACTGTGGTCA  CTAGACTCTT      780

GACATGTGAC  CCGTGTAACT  GAAAATTTCA  GTTTTTCACT  TTGTAAATCG  TAATCACATA      840

GAGTCTGACT  ACTGTGATGG  GTACCACACC  TCTACAGTAA  AGCAGGCACC  AGGGACTCCA      900

TGCAACTTCT  GGAGCGCGTG  TAGCAACAGC  ATGCGACCTC  AGGGATAGAT  GGTGGCAGGA      960

AGACAGTGGA  GTGATCTTGG  CAAGTCTGGG  GATTGCATAG  AGTAGACGGG  CTCTGCCTCA     1020

GGGACACCTA  ACGTTTCCAC  ACAGAACCCT  CCTAAGTCCT  GCCTACCACA  CAGAGAGGCC     1080

TCTCAGGATC  CAGCTGCAAT  GAGACAGCAC  TCGAGGGCCT  CAAACCTAGG  CTCCACCTAG     1140

CAACTGTCAC  CCTATGTGTC  AGTCAAGTCC  AGGCAGGTTC  AGAGAGGGGG  TGTGGAGCCA     1200

GAGTCACCCA  ATCCTGAAGG  GACAGATTTC  ACCATTTCCG  GGATGGGGCT  GTGGTGGGTC     1260

ACCGTGCAGC  CTCCAGCTTA  GGAGA ATG GGG TGG CTC CCA CTT CTG CTG CTT         1312
                         Met Gly Trp Leu Pro Leu Leu Leu Leu
                                            5

CTG GTA CAG TGT TCA AGG GCT CTT G GTGAGTGTCA CCCACCCTGA TCCCAGTCTG         1367
```

```
Leu Val Gln Cys Ser Arg Ala Leu G
 10              15
```

| | | | | |
|---|---|---|---|---|
| CCTTCACGAG | GGAGTTCACC | CCTGGTCTAC | ATAGCTATTC | TCATTGAGAG | TTTACTTTTC | 1427 |
| TTTGGGTCCG | GGATCAGTGA | CCTTGGCCTG | TTGAGCAGAG | CTGAGAAGGC | CTGGGAATTC | 1487 |
| AAATACACAC | AGTCTGATCA | GGACTACATT | AGAGCATACT | GTAGCCCAGA | GGCAGTCTTT | 1547 |
| CAACCAGAGA | AACTATCCAA | CCCAGAAGGC | AGGGCTCCTA | AGCCCGATGC | ACCACTGTAA | 1607 |
| CTTATGCCTT | TATTCTGGTG | AGAGGCCAGA | CTTGGGGCCT | TCCCCAGGAA | GTGTCCAAGC | 1667 |
| ATTCTCATCT | GAGGGGTGAG | AAGGGGCAAG | TGTCACAAGG | CCAACACACT | GTCACCCAAA | 1727 |
| TTCTCATGGA | GTGGATGTGG | TAGACCAGAG | CCCAGTGCCA | GGTCTCCTAG | CAGATGGGCA | 1787 |
| ATAATCACTG | TATCTGGGCC | TCCCCAGCTC | ACTGGCATGA | AGGGACTTGC | TGGGCCCTTG | 1847 |
| AAAATATACA | TAAGGCCTGC | CCCAAAGACC | TTGTATTAGA | TTCCCTAAAT | GAACAAAGA | 1907 |
| TAGGGTGTGT | TAAAGTACTA | ATGCGCTCAT | GCTCACCACG | CAG GG CAG CGC TCA | 1961 |

```
                                                    ly Gln Arg Ser
                                                            20
```

```
CCA CTG AAT GAC TTC CAG CTG TTC CGG GGC ACA GAG TTA AGG AAC CTG    2009
Pro Leu Asn Asp Phe Gln Leu Phe Arg Gly Thr Glu Leu Arg Asn Leu
         25                  30                  35

TTA CAC ACA GCG GTG CCG GGG CCA TGG CAG GAG GAT GTG GCA GAT GCT    2057
Leu His Thr Ala Val Pro Gly Pro Trp Gln Glu Asp Val Ala Asp Ala
     40                  45                  50

GAG GAG TGT GCT AGG CGC TGT GGG CCC CTT CTG GAC TGT CG GTGAGTGGCT  2108
Glu Glu Cys Ala Arg Arg Cys Gly Pro Leu Leu Asp Cys Ar
 55                  60                  65
```

| | | | | |
|---|---|---|---|---|
| AAGTAGCCTA | GATATGGCTG | AGGGCATGAG | AATCTGGGTT | GCCAGTTAAC | TTTGTGTCTG | 2168 |
| CCACCCCCCC | CCCCTTCTCC | AG G GCC TTC CAC TAC AAC ATG AGC AGC CAT | | | | 2218 |

```
              g Ala Phe His Tyr Asn Met Ser Ser His
                70                  75

GGT TGC CAG CTG CTG CCG TGG ACC CAG CAC TCG CTG CAC ACA CAG CTA    2266
Gly Cys Gln Leu Leu Pro Trp Thr Gln His Ser Leu His Thr Gln Leu
         80                  85                  90

TAC CAC TCG AGT CTG TGC CAT CTC TTC CAG AAG AAA G GCAAGTGGTG       2313
Tyr His Ser Ser Leu Cys His Leu Phe Gln Lys Lys A
         95                 100
```

| | | | | |
|---|---|---|---|---|
| GTGAGGAGGG | GAAACAGGCT | GAGTAACAGG | GGCCACGAGG | CTCAGGCCTG | TTGACCTTCC | 2373 |
| TCCATTGCTT | CCAG AT TAT GTG CGG ACC TGC ATT ATG GAC AAT GGG GTC | | | | | 2422 |

```
           sp Tyr Val Arg Thr Cys Ile Met Asp Asn Gly Val
                   110                 115

AGC TAC CGG GGC ACT GTG GCC AGG ACA GCT GGT GGC CTG CCC TGC CAA    2470
Ser Tyr Arg Gly Thr Val Ala Arg Thr Ala Gly Gly Leu Pro Cys Gln
        120                 125                 130

GCC TGG AGT CGC AGG TTC CCC AAT GAC CAC AA GTGAGTCAGA CACTTCAGGT   2522
Ala Trp Ser Arg Arg Phe Pro Asn Asp His Ly
        135                 140
```

| | | | | |
|---|---|---|---|---|
| CAGACCGTTA | GGCCTGAAGC | AGTATTCCCC | CAGTGTGCAC | TGTAGTAAGA | ATCTTTGTCT | 2582 |
| ACAG G TAT ACG CCC ACG CCA AAG AAT GGC CTG GAA GAG AAC TTC TGT | | | | | | 2629 |

```
     s Tyr Thr Pro Thr Pro Lys Asn Gly Leu Glu Glu Asn Phe Cys
            145                 150                 155

AGG AAC CCT GAT GGG GAT CCC AGA GGT CCC TGG TGC TAC ACA ACA AAC   2677
Arg Asn Pro Asp Gly Asp Pro Arg Gly Pro Trp Cys Tyr Thr Thr Asn
        160                 165                 170

CGC AGT GTG CGT TTC CAG AGC TGT GGC ATC AAA ACC TGC AGG GAG G     2723
Arg Ser Val Arg Phe Gln Ser Cys Gly Ile Lys Thr Cys Arg Glu A
        175                 180                 185
```

| | | | | |
|---|---|---|---|---|
| GTAAGCGGCT | GGGGTCAATC | AAGCCTAAGG | AGGGAGTGAT | AGGCCTGCCC | CCACTTAGAA | 2783 |

```
GTGCATTGGC CCTGTTTCCA G CT GTT TGT GTT CTG TGC AAC GGT GAG GAT         2833
                         la Val Cys Val Leu Cys Asn Gly Glu Asp
                            190             195

TAC CGT GGC GAG GTA GAC GTT ACA GAG TCA GGG CGG GAG TGT CAA CGC        2881
Tyr Arg Gly Glu Val Asp Val Thr Glu Ser Gly Arg Glu Cys Gln Arg
200             205                 210

TGG GAC CTG CAG CAC CCC CAC TCG CAC CCT TTC CAG CCT GAA AA             2925
Trp Asp Leu Gln His Pro His Ser His Pro Phe Gln Pro Glu Ly
215             220                 225

GTATGTAGGC AGAATCCTTA TTTTGAGGGT GGGGCTCAGC TCTACTGGGA CTGAGTCCCA      2985

GAGTCTTGTT ACTGCTTTCA G TTC CTA GAC AAA GAT CTG AAA GAC AAC TAT       3037
                       s Phe Leu Asp Lys Asp Leu Lys Asp Asn Tyr
                             230                 235

TGT CGT AAT CCG GAC GGA TCT GAG CGG CCC TGG TGC TAC ACC ACA GAC        3085
Cys Arg Asn Pro Asp Gly Ser Glu Arg Pro Trp Cys Tyr Thr Thr Asp
240             245                 250                 255

CCG AAT GTT GAG CGA GAA TTC TGC GAC CTG CCC AGT TGC G GTAGGCTGCA       3135
Pro Asn Val Glu Arg Glu Phe Cys Asp Leu Pro Ser Cys G
                260                 265

GGGTCAGGGT CTAGGAAGGA GCTTGGAAAA AACTGGCGGG CACGGTTCAA CTGGGAGAGG      3195

TACTAGGGAA GTTAGGCGTG GGTAGAGAGC AAAGCCTGCT GAGTACCAGA GACCAATTCC      3255

AGTTTTCGGT CAG GG CCT AAC CTG CCT CCG ACC GTC AAA GGA TCC AAG TCA      3306
               ly Pro Asn Leu Pro Pro Thr Val Lys Gly Ser Lys Ser
                      270                 275                 280

CAG CGG CGC AAC AAG GGC AAG GCT CTT AAC TGC TTC CGC GGA AAA GGT        3354
Gln Arg Arg Asn Lys Gly Lys Ala Leu Asn Cys Phe Arg Gly Lys Gly
        285                 290                 295

GAA GAC TAT CGA GGC ACA ACC AAT ACC ACC TCT GCG GGC GTG CCC TGC        3402
Glu Asp Tyr Arg Gly Thr Thr Asn Thr Thr Ser Ala Gly Val Pro Cys
300                 305                 310

CAG CGG TGG GAT GCG CAG AGT CCA CAC CAG CAC CGC TTT GTG CCA GAG        3450
Gln Arg Trp Asp Ala Gln Ser Pro His Gln His Arg Phe Val Pro Glu
        315                 320                 325

AAA TAT GCT TGC AA GTGAGGTGAC AGGCCGGAGC AGGGAGAGTG CACCTGTGGG         3504
Lys Tyr Ala Cys Ly
330

TGGAGGCAGA GCGTATGCGA AGGTGGGACC TGGGGGCGGA GTCAGAGGTT CCAGCCTACT      3564

GCGGGTTGGC TGGTGGGCTA GGTGGGACCC CACTCTCGAT AAGGGAAGTG ACTACTCAG       3623

G GAC CTT CGT GAG AAT TTC TGC CGG AAT CCT GAT GGC TCC GAG GCG          3669
s Asp Leu Arg Glu Asn Phe Cys Arg Asn Pro Asp Gly Ser Glu Ala
    335                 340                 345

CCT TGG TGC TTC ACA TCT CGA CCT GGT TTG CGC ATG GCC TTC TGC CAC        3717
Pro Trp Cys Phe Thr Ser Arg Pro Gly Leu Arg Met Ala Phe Cys His
350                 355                 360                 365

CAG ATC CCA CGC TGC ACT GAA GAA CTG GTG CCA GAG G GTGAGGCTGG           3764
Gln Ile Pro Arg Cys Thr Glu Glu Leu Val Pro Glu G
        370                 375

AGCGGGGGTA CAGAATCTGG GCAGGAATCA ACCCAGGGCT GACCACCGCT CTTGCCTGCC      3824

CACCACAG GA TGC TAC CAC GGC TCA GGT GAA CAG TAT CGT GGC TCA GTC        3873
         ly Cys Tyr His Gly Ser Gly Glu Gln Tyr Arg Gly Ser Val
                380                 385                 390

AGC AAG ACG CGC AAG GGC GTT CAG TGC CAG CAC TGG TCC TCT GAG ACA        3921
Ser Lys Thr Arg Lys Gly Val Gln Cys Gln His Trp Ser Ser Glu Thr
        395                 400                 405

CCG CAC AAG CCA CA GTGAGTGTGT GCTATGTGCA GATAGGGCCT TAACTCTAGG         3975
Pro His Lys Pro Gl
410
```

| | |
|---|---:|
| GCAGAATACC TTAAGTTCTT GTGAGCCTAA AGAGGGTCTA AGTGGCCTGA TGTGTCCCCC | 4035 |

```
TACCTCCTGC CCCTACATCT AG A TTT ACA CCC ACC TCG GCA CCG CAG GCG                            4085
                          n Phe Thr Pro Thr Ser Ala Pro Gln Ala
                            415                             420

GGA CTG GAG GCC AAC TTC TGC AGG AAT CCT GAT GGG GAT AGC CAT GGG                           4133
Gly Leu Glu Ala Asn Phe Cys Arg Asn Pro Asp Gly Asp Ser His Gly
            425                 430                 435

CCC TGG TGC TAT ACC TTG GAC CCG GAT ATC CTG TTT GAC TAC TGT GCC                           4181
Pro Trp Cys Tyr Thr Leu Asp Pro Asp Ile Leu Phe Asp Tyr Cys Ala
        440                 445                 450

CTA CAG CGC TGT G GTTAGTGCTT AAGACTTCCC CTTGTCTGGG TTTCAAACCT                             4234
Leu Gln Arg Cys A
    455

CACCTCCATA GACTGGCTCC CTTAACCTGA GTGAACTTGA TCTTGCAG AT GAT GAC                           4290
                                                         sp Asp Asp
                                                                460

CAG CCA CCA TCC ATT CTG GAC CCC CCA G GTATGGGGTT GGGCCAATTG                               4338
Gln Pro Pro Ser Ile Leu Asp Pro Pro A
            465

TGGGTACACA GTCTTTGACC CTGACCCTCA CTGAAGGTTT CATCCTGCCC CATCCCCAG                          4397

AC CAG GTG GTG TTT GAA AAG TGT GGC AAG AGA GTT GAC AAG AGT AAT                            4444
sp Gln Val Val Phe Glu Lys Cys Gly Lys Arg Val Asp Lys Ser Asn
                475                 480                 485

AAA CTT CGT GTG GTG GGA GGC CAT CCT GGG AAC TCC CCA TGG ACG GTC                           4492
Lys Leu Arg Val Val Gly Gly His Pro Gly Asn Ser Pro Trp Thr Val
            490                 495                 500

AGC TTG CGG AAT CG GTGAGGCCTA AGCGCTTATC TCAAGGAGTG GAGGCTGGAA                            4546
Ser Leu Arg Asn Ar
            505

ACTCTGTGGC TTTATCAGTA GAAGATGGAT GCCTGGCCTT GTACCAAAAG GTCCTTGTCA                         4606

GAAATGACAG TCTAGCATGT GTCCCAGGAC TCAGTGTGGC TTCTCATCTT TACTCCTCTA                         4666

G A CAG GGC CAG CAT TTC TGT GGG GGC TCC CTA GTG AAG GAG CAG TGG                           4713
  g Gln Gly Gln His Phe Cys Gly Gly Ser Leu Val Lys Glu Gln Trp
            510                 515                 520

GTA CTG ACT GCC CGG CAA TGC ATC TGG TCA TG GTGAGCAGAC TGGGGACTCC                          4765
Val Leu Thr Ala Arg Gln Cys Ile Trp Ser Cy
            525                 530

TAGCCTACCT CTCCCTGCCA TTGTCTGTCC CACAAGCAAA CTAAATTGTG ACAGCTGATT                         4825

GGGAGTCAAG CATGAACTAG CAGAGTCTCT TTCTCCCAG C CAC GAA CCT CTC ACA                          4880
                                          s His Glu Pro Leu Thr
                                                        535

GGA TAC GAG GTA TGG TTG GGT ACA ATT AAC CAG AAC CCA CAG CCT GGA                           4928
Gly Tyr Glu Val Trp Leu Gly Thr Ile Asn Gln Asn Pro Gln Pro Gly
            540                 545                 550

GAG GCA AAC CTG CAG AGG GTC CCA GTG GCC AAG GCA GTG TGC GGC CCT                           4976
Glu Ala Asn Leu Gln Arg Val Pro Val Ala Lys Ala Val Cys Gly Pro
            555                 560                 565

GCA GGC TCC CAG CTT GTT CTG CTC AAG CTG GAG AG GTATGTGGAT                                 5021
Ala Gly Ser Gln Leu Val Leu Leu Lys Leu Glu Ar
570             575                 580

GTGTTGAGAG GGTGTGAGGC AGGGCTAGCC TCATGGTCAT AGGTCCTGAA AACCCTCATT                         5081

CCCACTAAAG A CCT GTG ATC CTG AAC CAT CAC GTG GCC CTG ATT TGC CTG                          5131
             g Pro Val Ile Leu Asn His His Val Ala Leu Ile Cys Leu
                            585                 590

CCT CCT GAA CAG TAT GTG GTA CCT CCA GGG ACC AAG TGT GAG ATC GCA                           5179
Pro Pro Glu Gln Tyr Val Val Pro Pro Gly Thr Lys Cys Glu Ile Ala
            595                 600                 605
```

| | |
|---|---|
| GGC TGG GGT GAA TCC ATC G GTAAGAGCAC AGTGCATAGA CATGGACTGC<br>Gly Trp Gly Glu Ser Ile G<br>615 | 5228 |
| TATGGGCCGG GAGGTCCAGC ACTGGTTTTG GCTCAAGGGT CCCCTCCTTA TCATTGTCTG | 5288 |
| TACTTCAG GT ACA AGC AAT AAC ACA GTC CTT CAT GTG GCC TCG ATG AAT<br>ly Thr Ser Asn Asn Thr Val Leu His Val Ala Ser Met Asn<br>620 625 630 | 5337 |
| GTC ATC TCC AAC CAG GAA TGT AAC ACG AAG TAC CGA GGA CAC ATA CAA<br>Val Ile Ser Asn Gln Glu Cys Asn Thr Lys Tyr Arg Gly His Ile Gln<br>635 640 645 | 5385 |
| GAG AGT GAG ATA TGC ACC CAG GGA CTG GTG GTC CCT GTG GGG GCT TGT<br>Glu Ser Glu Ile Cys Thr Gln Gly Leu Val Val Pro Val Gly Ala Cys<br>650 655 660 | 5433 |
| GAG GTCAGTGGGA GAGCCCCTGG GCCAGCCTGG GAAGGGCTTG GGAGCTGAAA<br>Glu | 5486 |
| TTATAGTACT TGATTGCCAA GGGGGTGGGA TGTCAGGAGA GGGTAGTCAC TGCCGAGGTC | 5546 |
| CAGAGCCTTC ACCCGTTTTT CTACCTGCCA G GGT GAC TAC GGG GGC CCA CTT<br>Gly Asp Tyr Gly Gly Pro Leu<br>665 670 | 5598 |
| GCC TGC TAT ACC CAT GAC TGC TGG GTC CTA CAG GGA CTT ATC ATC CCG<br>Ala Cys Tyr Thr His Asp Cys Trp Val Leu Gln Gly Leu Ile Ile Pro<br>675 680 685 | 5646 |
| AAC AGA GTG TGT GCA CGG CCC CGC TGG CCA GCT ATC TTC ACA CGG GTG<br>Asn Arg Val Cys Ala Arg Pro Arg Trp Pro Ala Ile Phe Thr Arg Val<br>690 695 700 | 5694 |
| TCT GTG TTC GTG GAC TGG ATT AAC AAG GTC ATG CAG CTG GAG<br>Ser Val Phe Val Asp Trp Ile Asn Lys Val Met Gln Leu Glu<br>705 710 715 | 5736 |
| TAGGCCTGCT TTTGAGCCCT TAGAGATGTC AAGACTTCTC AAACATAAAG CGGCCTTTTC | 5796 |
| TCTCTGTCTG TATAGAGTGC TTCTTAGTTTCTGT CTCTAGGGAA GGTGTTGACT CCTTGC | 5856 |
| AAGAGGCTGT GTGGCTTAAG ACCAGCACAC TCTAGGCTAA GTGCTCTGAT CCCAGAACAA | 5916 |
| CTTCAAAAGG TATGTACTGT GTGTGGGCAG GGTGCACCAT CTTCCAGAGG CACTCCTGGG | 5976 |
| AATGCAAGGA CAGTGCAGAA GTTCCCAGCC CATGGACCAG AGCAGAAAGA GTGATGTAGG | 6036 |
| TCTACACCAG TCCCGTTTGG CTAGGACAGG CAGGGGTTGA GTCTCTCATG GCTTCTCTCT | 6096 |
| GTCACATGAC AGGGATGAAT ACACTGTGGA TATCAAACCA AGGACCTAGG GTTTCTGAAC | 6156 |
| CCCAAGGTAG AGGCTGGGGC TGGGGATGGC TTGTACAAAG TACCAGCACA GACCAGGCTC | 6216 |
| TGTGTCCTCC TTTATTATGA TTAGAGTCCA TAGTCCTCTG CCCACTCATT CGGAGTCCAG | 6276 |
| AGCCCAGGAA ACCTCTAGGC AGTTCTGCCA GATCCTGGGG CTTACCGAAG AGCAAAGTTC | 6336 |
| GAGACGGACT GCCCAGCTCA CAAAGAGCAA CAGGGCTTCA GCTGCCCAAG TGTGTGTGTA | 6396 |
| GCCAAAGCAC AGTGTTCATG AAGCTGTCTG ATTCCACCTC CACCTCTGAC AGCGCATGGG | 6456 |
| TGCTCTTGGG ATACAGCAGG AGCCTGTATG AGCAGCAACA CATGACATTG GAGGGTCCTG | 6516 |
| TCCTGTTTAC CTGCCACCAG CTGCCCAACT ATCCTGTACA CTCACCGGAC AGGCACATTC | 6576 |
| CGGGCCTTGA GGCATGGTA ATACTCCAGA CCCTGCTTGA AGGGTACACG CCGGTCCTCC | 6636 |
| TGGCCCAGCA TCAGTAACAC TGGTGTCTTT ACCTAGGTGT ATGGGAGGCA AGGAGCTGTG | 6696 |
| GCGAGCTGAG CTCTGGACTC TGGAGGAATG GGTGGCACAA GGATACCTGG GTACC | 6751 |

( 2 ) INFORMATION FOR SEQ ID NO:6:

( i ) SEQUENCE CHARACTERISTICS:
( A ) LENGTH: 6100 base pairs
( B ) TYPE: nucleic acid 5,606,029

43                                                                                  44
-continued

```
        ( C ) STRANDEDNESS: single
        ( D ) TOPOLOGY: linear ( i i ) MOLECULE TYPE: genomic DNA ( i v ) ANTI-SENSE: no ( v i ) ORIGINAL SOURCE:
            ( A ) ORGANISM: human
            ( D ) DEVELOPMENTAL STAGE: fetal
            ( F ) TISSUE TYPE: liver ( v i i ) IMMEDIATE SOURCE:
            ( A ) LIBRARY: genomic
            ( B ) CLONE: L5/3

( v i i i ) POSITION IN GENOME:
            ( A ) CHROMOSOME/SEGMENT: human 3p21/D3F15S2

( i x ) FEATURE:
            ( C ) IDENTIFICATION METHOD: experimental
            ( D ) OTHER INFORMATION: This is the combined sequence of the
                  entire gene from two different recombinant phage isolates
                  ( L 5  &  L 5 / 3 ).

( x ) PUBLICATION INFORMATION:
            ( K ) RELEVANT RESIDUES IN SEQ ID NO:6: FROM 1 TO 6100

( x i ) SEQUENCE DESCRIPTION: SEQ ID NO:6:
```

| | | | | | |
|---|---|---|---|---|---|
| CTGCAGAGGG | GTTTCACCCC | AACCCCAGGG | CACCTCAAGT | GTCCCCACCA | AACCTTCCTA | 60 |
| ACACCTGTCC | ACTAAGCTGT | ACTAGGCCCT | TGCAACTGAC | CTATGGGACC | CTGAGGCCTG | 120 |
| GCCCCTCATG | GCTCCTGTCA | CCAGGTCTCA | GGTCAGGGTC | CAGCAGGGCC | CTGAGCTGAC | 180 |
| GTGTGGAGCC | AGAGCCACCC | AATCCCGTAG | ACAGGTTTCA | CAACTTCCCG | ATGGGGCTG  | 240 |
| TGGTGGGTCA | CAGTGCAGCC | TCCAGCCAGA | AGG ATG GGG TGG CTC CCA CTC CTG | | | 294 |
| | | | Met Gly Trp Leu Pro Leu Leu | | | |
| | | | 5 | | | |

```
CTG CTT CTG ACT CAA TGC TTA GGG GTC CCT G GTAAGTGCCC CCAACCCTGA         345
Leu Leu Leu Thr Gln Cys Leu Gly Val Pro G
             10              15
```

| | | | | | |
|---|---|---|---|---|---|
| TCCCCATCTG | CCTTCAGGAG | GGGGTTGGCC | CCATTCTCCT | ATTCTAGGAT | GAGAAAAAAG | 405 |
| TCGGGAGCAG | AGGCTCAGTG | GGCATGGGGC | AGTGACCTTG | CCCTCTTGAG | CACAGCTGGG | 465 |
| AAGCCCTAGG | AACACATAGA | CATTGCCCAC | TTAGGCCTCT | ATTAGCACGT | CTGCTCTAGC | 525 |
| ACTGAAGCAG | TGTCAGGACC | ACACAGATGC | ACGCACACAG | CAGGCAGTGA | CCCCTCCTGA | 585 |
| GCCTGATCTA | CCCCTCTAAC | CTAGCATATG | CCTTTGTGCA | GGTGAGAGCC | CAGATTTGGA | 645 |
| GTCTGAATGC | CTAGCCAGGG | CCCTTGGCTG | GGTAATGTGA | TGGCTCTGAG | CCTTAGCATT | 705 |
| CTCATTTGAG | AGATGAGGTG | GGGCAAGCTT | CATCACCCAC | TGCTCTCACA | GAGCGTATGT | 765 |
| GTTAGATCTG | AGCCCGGTGC | CTGGGCCACT | AAACAGAGGC | ACCGGTGATA | ACTACCAAGT | 825 |
| CTGGGCCTGC | TTCCCAGGGG | AAATTTTTTT | CACAAGTATC | TGTGCAGGGG | GCTAGACTGG | 885 |
| CCCTTGAAAG | TGCATACAGG | GTCCATCCCA | GAAGCTTGTA | GCTTTGATCC | CCTGAATGAA | 945 |
| CAAAGTGTGG | ACATGCCAAT | ACACATTACT | GACATGTATG | CCCACCTGAC | CTGCACCCAC | 1005 |

```
TCATGCCTAC TCTGCAG GG CAG CGC TCG CCA TTG AAT GAC TTC CAA GTG CTC         1057
                ly Gln Arg Ser Pro Leu Asn Asp Phe Gln Val Leu
                   20                        25

CGG GGC ACA GAG CTA CAG CAC CTG CTA CAT GCG GTG GTG CCC GGG CCT         1105
Arg Gly Thr Glu Leu Gln His Leu Leu His Ala Val Val Pro Gly Pro
30            35               40                  45

TGG CAG GAG GAT GTG GCA GAT GCT GAA GAG TGT GCT GGT CGC TGT GGG         1153
Trp Gln Glu Asp Val Ala Asp Ala Glu Glu Cys Ala Gly Arg Cys Gly
                50              55                  60
```

| | |
|---|---|
| CCC TTA ATG GAC TGC CG GTGAGTGGCC ACTGGGCTAG ATAAGACTGG<br>Pro Leu Met Asp Cys Ar<br>65 | 1200 |
| GGGCAGGGAA GCCTGGGCTG TGGCGTTACC CTGTGCCTTC TTCTCTCCAG G GCC TTC<br>g Ala Phe | 1257 |
| CAC TAC AAC GTG AGC AGC CAT GGT TGC CAA CTG CTG CCA TGG ACT CAA<br>His Tyr Asn Val Ser Ser His Gly Cys Gln Leu Leu Pro Trp Thr Gln<br>70                      75                      80                      85 | 1305 |
| CAC TCG CCC CAC ACG AGG CTG CGG CGT TCT GGG CGC TGT GAC CTC TTC<br>His Ser Pro His Thr Arg Leu Arg Arg Ser Gly Arg Cys Asp Leu Phe<br>              90                          95                          100 | 1353 |
| CAG AAG AAA G GCAAGTGGGG GTGGAGAGGG GCAGGGTGGG AGACAGGGGA<br>Gln Lys Lys A | 1403 |
| CCTCAGCCCA AGTTGATCTT CTGTCTCTTG CTCCCAG AC TAC GTA CGG ACC TGC<br>sp Tyr Val Arg Thr Cys<br>110 | 1457 |
| ATC ATG AAC AAT GGG GTT GGG TAC CGG GGC ACC ATG GCC ACG ACC GTG<br>Ile Met Asn Asn Gly Val Gly Tyr Arg Gly Thr Met Ala Thr Thr Val<br>115                      120                      125 | 1505 |
| GGT GGC CTG CCC TGC CAG GCT TGG AGC CAC AAG TTC CCG AAT GAT CAC<br>Gly Gly Leu Pro Cys Gln Ala Trp Ser His Lys Phe Pro Asn Asp His<br>130                      135                      140 | 1553 |
| AA GTGAGACAAA CACCTTCCCT CCGTCCCGGC CTGGGGCTTC CCCCAGCACA<br>Ly | 1605 |
| CACTATAGTG ATGCTCTGGG CCCTCAG G TAC ACG CCC ACT CTC CGG AAT GGC<br>s Tyr Thr Pro Thr Leu Arg Asn Gly<br>145                      150 | 1657 |
| CTG GAA GAG AAC TTC TGC CGT AAC CCT GAT GGC GAC CCC GGA GGT CCT<br>Leu Glu Glu Asn Phe Cys Arg Asn Pro Asp Gly Asp Pro Gly Gly Pro<br>155                      160                      165 | 1705 |
| TGG TGC TAC ACA ACA GAC CCT GCT GTG CGC TTC CAG AGC TGC GGC ATC<br>Trp Cys Tyr Thr Thr Asp Pro Ala Val Arg Phe Gln Ser Cys Gly Ile<br>170                      175                      180 | 1753 |
| AAA TCC TGC CGG GAG G GTAAGCGGCG CCGGGTCAAG CTGGGAGAGT GGAGACAAGC<br>Lys Ser Cys Arg Glu A<br>185 | 1809 |
| CCACGTCCAT CCACGAACCC ACTGGCTCTT TGTCTCCAG CC GCG TGT GTC TGG TGC<br>la Ala Cys Val Trp Cys<br>190 | 1865 |
| AAT GGC GAG GAA TAC CGC GGC GCG GTA GAC CGC ACG GAG TCA GGG CGC<br>Asn Gly Glu Glu Tyr Arg Gly Ala Val Asp Arg Thr Glu Ser Gly Arg<br>195                      200                      205                      210 | 1913 |
| GAG TGC CAG CGC TGG GAT CTT CAG CAC CCG CAC CAG CAC CCC TTC GAG<br>Glu Cys Gln Arg Trp Asp Leu Gln His Pro His Gln His Pro Phe Glu<br>              215                      220                      225 | 1961 |
| CCG GGC AA GTACGCGTAG GCGGTATCGG CGTCCTGGGG GCCGGGCTAG GAAGGTCCA<br>Pro Gly Ly | 2019 |
| GGACTCCAGG GGCAGGGCTC CGTGTAGGGC AATTGGGCGG GGCCAGATAA GCCAGAGTCC | 2079 |
| CAGGGTCTTG TTCACGCCCC ATTACCGCCC CCAG G TTC CTC GAC CAA GGT CTG<br>s Phe Leu Asp Gln Gly Leu<br>230                      235 | 2132 |
| GAC GAC AAC TAT TGC CGG AAT CCT GAC GGC TCC GAG CGG CCA TGG TGC<br>Asp Asp Asn Tyr Cys Arg Asn Pro Asp Gly Ser Glu Arg Pro Trp Cys<br>240                      245                      250 | 2180 |
| TAC ACT ACG GAT CCG CAG ATC GAG CGA GAG TTC TGT GAC CTC CCC CGC<br>Tyr Thr Thr Asp Pro Gln Ile Glu Arg Glu Phe Cys Asp Leu Pro Arg<br>255                      260                      265 | 2228 |
| TGC G GTAGGCGGCG GGGACCAGGC CTGGGAGGGT ACCTGGGAAC CTTGGGGAGG<br>Cys G | 2282 |

```
GGCGTGGCTT GGCCGGGGAG GTAAGAGGGG CTGGGCGTGA CCTGAGAGCA TACCCCGTGG                                        2342

AGTACCGTAC ACCTGGGAAA GGCGGGTTTG GTCCCAGCCC CAGAGGGATC TCAGCTCTCG                                        2402

CTCGGGGCCC GACCTATCTC GGTCCATCTA AG GG TCC GAG GCA CAG CCC CGC                                           2454
                                      ly Ser Glu Ala Gln Pro Arg
                                         270                 275

CAA GAG GCC ACA ACT GTC AGC TGC TTC CGC GGG AAG GGT GAG GGC TAC                                          2502
Gln Glu Ala Thr Thr Val Ser Cys Phe Arg Gly Lys Gly Glu Gly Tyr
                280                 285                 290

CGG GGC ACA GCC AAT ACC ACC ACT GCG GGC GTA CCT TGC CAG CGT TGG                                          2550
Arg Gly Thr Ala Asn Thr Thr Thr Ala Gly Val Pro Cys Gln Arg Trp
            295                 300                 305

GAC GCG CAA ATC CCT CAT CAG CAC CGA TTT ACG CCA GAA AAA TAC GCG                                          2598
Asp Ala Gln Ile Pro His Gln His Arg Phe Thr Pro Glu Lys Tyr Ala
        310                 315                 320

TGC AA GTGAGGTGGG GGGGGGGGGC GGGCGTTGGG ACGTGCTGCT GCGGGTGAGA                                            2653
Cys Ly

CGGGAGGAAG GTAGTCACGG GCTCAAGGCT GGAGGCTGGC GGGCTAGGGC TGAGTGGAGC                                        2713

GCCTGCTTAG A GAC CTT CGG GAG AAC TTC TGC CGG AAC CCC GAC GGC TCA                                         2763
           s Asp Leu Arg Glu Asn Phe Cys Arg Asn Pro Asp Gly Ser
                                  330                 335

GAG GCG CCC TGG TGC TTC ACA CTG CGG CCC GGC ATG CGC GCG GCC TTT                                          2811
Glu Ala Pro Trp Cys Phe Thr Leu Arg Pro Gly Met Arg Ala Ala Phe
340                 345                 350

TGC TAC CAG ATC CGG CGT TGT ACA GAC GAC GTG CGG CCC CAG G                                                2854
Cys Tyr Gln Ile Arg Arg Cys Thr Asp Asp Val Arg Pro Gln A
355                 360                 365

GTGAGGCCCA AGCTTGGGGG CTACAGAGCC GGGCTGGAAG CTGGAACCGG AGGCCGGGGC                                        2914

GAGGTCTCGG CCTGATGGCT GCCCGCACCC GCCACAG AC TGC TAC CAC GGC GCA                                          2968
                                        sp Cys Tyr His Gly Ala
                                           370

GGG GAG CAG TAC CGC GGC ACG GTC AGC AAG ACC CGC AAG GGT GTC CAG                                          3016
Gly Glu Gln Tyr Arg Gly Thr Val Ser Lys Thr Arg Lys Gly Val Gln
                375                 380                 385

TGC CAG CGC TGG TCC GCT GAG ACG CCG CAC AAG CCG CA GTGAGTCCCT                                            3064
Cys Gln Arg Trp Ser Ala Glu Thr Pro His Lys Pro Gl
                395                 400

GGTGCTCCCG GCCCCGCCAG GGCCCTAACC CTGGGGCGGC ATGCTTTGGT GTCTGGGACC                                        3124

AGAGCCTGGA AATGGTTGAG ACTACCCTGC CACGATTTTG CTCCCGCTTC CGCCTAG G                                         3182
                                                                n

TTC ACG TTT ACC TCC GAA CCG CAT GCA CAA CTG GAG GAG AAC TTC TGC                                          3230
Phe Thr Phe Thr Ser Glu Pro His Ala Gln Leu Glu Glu Asn Phe Cys
405                 410                 415

CGG AAC CCA GAT GGG GAT AGC CAT GGG CCC TGG TGC TAC ACG ATG GAC                                          3278
Arg Asn Pro Asp Gly Asp Ser His Gly Pro Trp Cys Tyr Thr Met Asp
420                 425                 430                 435

CCA AGG ACC CCA TTC GAC TAC TGT GCC CTG CGA CGC TGC G GTGAGCACTA                                         3328
Pro Arg Thr Pro Phe Asp Tyr Cys Ala Leu Arg Arg Cys A
                440                 445

GTGACGCTTC CCCCATGACC CTGCCTCAGC CCCCACCCAA AGGCTGGCTC CCTTAACCCC                                        3388

AGTGAACTTT GTCTTTCAG CT GAT GAC CAG CCG CCA TCA ATC CTG GAC CCC                                          3439
                   la Asp Asp Gln Pro Pro Ser Ile Leu Asp Pro
                      450                 455

CCA G GTTAGGAGTT GGGCCAGTTA TGGGTCAGGC CCTTTAGCCC ACGACATCCA                                             3493
Pro A

CACAGTCTGG GTTTCATCCA GCCCACCCCA TCCTACAG AC CAG GTG CAG TTT GAG                                         3548
                                         sp Gln Val Gln Phe Glu
```

```
                                                                          465
AAG TGT GGC AAG AGG GTG GAT CGG CTG GAT CAG CGG CGT TCC AAG CTG             3596
Lys Cys Gly Lys Arg Val Asp Arg Leu Asp Gln Arg Arg Ser Lys Leu
            470                 475                 480

CGC GTG GTT GGG GGC CAT CCG GGC AAC TCA CCC TGG ACA GTC AGC TTG             3644
Arg Val Val Gly Gly His Pro Gly Asn Ser Pro Trp Thr Val Ser Leu
            485                 490                 495

CGG AAT CG GTGAGGCACA ACTGCCTGTC TCCCACAGAG AGGAGCTGAG GTTGTGTCCT           3702
Arg Asn Ar
        500

CTGTGGTTAT CCACTGGGGC TGGGAATCTA TCCGTGCCCC TTGAGAGGTC CTAGCCAAGA           3762

AGATGGCAGG TCTTACGAAT CTGTCCCAGG AGTCTGTTAC CTGTCCTAAT TCCCCACTCC           3822

TCTAG G CAG GGC CAG CAT TTC TGC GGG GGG TCT CTA GTG AAG GAG CAG             3870
      g Gln Gly Gln His Phe Cys Gly Gly Ser Leu Val Lys Glu Gln
                          505                 510                 515

TGG ATA CTG ACT GCC CGG CAG TGC TTC TCC TCC TG GTGAGCCTCC                   3915
Trp Ile Leu Thr Ala Arg Gln Cys Phe Ser Ser Cy
             520                 525

CTTGTGTTTG GGACCCAGT CTCATCCCAC CTTCCCCCTT CCCCAGGCAA GCTAACAAGT            3975

GAGCCTTGGG GCAATGGACT GAGAGTCACA AATGACCTAG CAGAGCTTCT CTCCCAG C            4033
                                                                  s
CAT ATG CCT CTC ACG GGC TAT GAG GTA TGG TTG GGC ACC CTG TTC CAG             4081
His Met Pro Leu Thr Gly Tyr Glu Val Trp Leu Gly Thr Leu Phe Gln
            530                 535                 540

AAC CCA CAG CAT GGA GAG CCA AGC CTA CAG CGG GTC CCA GTA GCC AAG             4129
Asn Pro Gln His Gly Glu Pro Ser Leu Gln Arg Val Pro Val Ala Lys
545                 550                 555

ATG GTG TGT GGG CCC TCA GGC TCC CAG CTT GTC CTG CTC AAG CTG GAG             4177
Met Val Cys Gly Pro Ser Gly Ser Gln Leu Val Leu Leu Lys Leu Glu
560                 565                 570                 575

AG GTATGTGGAC AACCTGGGAG GGTGTGAGGT GGGGCTGGGC CTTGTGGCCT                   4229
Ar

CAGACCCTGA GTGCCCCCAT TCTTGCTAAA G A TCT GTG ACC CTG AAC CAG CGT            4282
                                 g Ser Val Thr Leu Asn Gln Arg
                                                     580

GTG GCC CTG ATC TGC CTG CCC CCT GAA TGG TAT GTG GTG CCT CCA GGG             4330
Val Ala Leu Ile Cys Leu Pro Pro Glu Trp Tyr Val Val Pro Pro Gly
585                 590                 595

ACC AAG TGT GAG ATT GCA GGC TGG GGT GAG ACC AAA G GTAAGAGCAC                4377
Thr Lys Cys Glu Ile Ala Gly Trp Gly Glu Thr Lys G
600                 605                 610

AGTGCACAGG ACTGCTGGTG GCCAGGAGGC CAGCCCTGGA TCTTCCTGCA GGACCCTCTC           4437

CCTCTCCCCA TTCCCCTCAC TGCAG GT ACG GGT AAT GAC ACA GTC CTA AAT              4488
                            ly Thr Gly Asn Asp Thr Val Leu Asn
                                                 615             620

GTG GCC TTG CTG AAT GTC ATC TCC AAC CAG GAG TGT AAC ATC AAG CAC             4536
Val Ala Leu Leu Asn Val Ile Ser Asn Gln Glu Cys Asn Ile Lys His
            625                 630                 635

CGA GGA CGT GTG CGG GAG AGT GAG ATG TGC ACT GAG GGA CTG TTG GCC             4584
Arg Gly Arg Val Arg Glu Ser Glu Met Cys Thr Glu Gly Leu Leu Ala
            640                 645                 650

CCT GTG GGG GCC TGT GAG GTTGGTGGCA GGGCCTGGGC AGCCCTGGAA                    4632
Pro Val Gly Ala Cys Glu
            655

GTATGGGGGG CTAGAAATGA ACTATTTTAT CATGAAGCAG GCTAGTCATT GCTGTGGCCC           4692

GGGGCCTCAT CAGTTCTCCT ACCTGCCAG GGT GAC TAC GGG GGC CCA CTT GCC             4745
                                Gly Asp Tyr Gly Gly Pro Leu Ala
```

-continued

| | | | | | | | 660 | | | | | 665 | | | |
|---|---|---|---|---|---|---|---|---|---|---|---|---|---|---|---|
| TGC | TTT | ACC | CAC | AAC | TGC | TGG | GTC | CTG | GAA | GGA | ATT | ATA | ATC | CCC | AAC | 4793 |
| Cys | Phe | Thr | His | Asn | Cys | Trp | Val | Leu | Glu | Gly | Ile | Ile | Ile | Pro | Asn | |
| | | | 670 | | | | | 675 | | | | | 680 | | | |
| CGA | GTA | TGC | GCA | AGG | TCC | CGC | TGG | CCA | GCT | GTC | TTC | ACG | CGT | GTC | TCT | 4841 |
| Arg | Val | Cys | Ala | Arg | Ser | Arg | Trp | Pro | Ala | Val | Phe | Thr | Arg | Val | Ser | |
| | | 685 | | | | | 690 | | | | | 695 | | | | |
| GTG | TTT | GTG | GAC | TGG | ATT | CAC | AAG | GTC | ATG | AGA | CTG | GGT | TAGGCCCAGC | | | 4890 |
| Val | Phe | Val | Asp | Trp | Ile | His | Lys | Val | Met | Arg | Leu | Gly | | | | |
| | 700 | | | | 705 | | | | | 710 | | | | | | |

| | | | | | |
|---|---|---|---|---|---|
| CTTGATGCCA | TATGCCTTGG | GGAGGACAAA | ACTTCTTGTC | AGACATAAAG | CCATGTTTCC | 4950 |
| TCTTTATGCC | TGTACAGATG | CTTCTTAGCC | TTTGCTTCCA | GGAAATGTGT | CAGTGACTCC | 5010 |
| TTGCTAGGGC | TCGGGTGGCT | TGAGCCCAGC | ACACCCTGGG | CTAGGTGATC | TGTCCAGCCT | 5070 |
| AGGGGCTTCC | CCAACCAAGG | CAATGTCCCT | GGGACTACTT | TTGCCCATGG | GTGCCGTGGA | 5130 |
| AAGACAGGGC | CTCACACTAG | TCCTCCAGAC | ATACTCTTGG | GAAGGGTGGT | ACAGAGTAGT | 5190 |
| TGCTAATGGA | AGGGGCTGCA | GCAGGGAAGC | TAGGCTGGTA | CAGAGTCCTG | GTTGCCAGGA | 5250 |
| CAGGCAGAGG | CTAAGCCTCT | CACTGTTCCC | TCCCTTCTCA | CACTGGAGGC | AGATGAAGCC | 5310 |
| CTTGTGGCTG | CCACACCCAG | AACCTAGGGT | CTCTGCACCC | CAGAGTGGGA | GGTGGGGTTG | 5370 |
| GGGATGGTTT | GGTACAAAGT | ACCAGCAGGA | ACCAGGCTCT | GTGTCCTAAT | TTATTATGAC | 5430 |
| TACATAGCCC | ACATTCCTCT | GCCCATGCAT | CCGTGGAGTC | CAGAGCCCAG | AAAGCCTCCT | 5490 |
| GCTGCCCTGC | CAGACCGTTG | AGCTCCTCAA | GAGGAAGTGT | GGCACAGGCT | GATCAGCTCA | 5550 |
| TGCAGAATGG | CAGGGCTTCA | GCTGCCCAAG | TGTGTGCGTA | GCCAGAGCAC | AGCATTCATG | 5610 |
| AAGCTGTCTG | ACTCCACCTC | CACCTCTGAT | AATGCGTGGG | TGCTTTTGGG | ATAGAGCAGG | 5670 |
| AGCCTGTAGG | GATTAGTCAG | CAACATTTAA | GGTTGGAGGG | TCCTCCTGTG | CTCACCTGCC | 5730 |
| CACCAGCTGC | CAGGGCCTTC | ATGCTGCACT | CACCGAACAG | GCACATTCCG | GGTCTTGAGG | 5790 |
| GCACGGTAAT | ACTCCATGCC | CTGCTTGAAG | GGCACACGCC | GGTCCTCCTG | GCCCAACATC | 5850 |
| AGTAACAGTG | GTGTCTTCAC | CTGGGTGTTT | GGGGAAGAGT | GGGGAGCTGT | GTTGAGCTGG | 5910 |
| GCCCTGGATT | CTGGATGGAT | GGGCAGCACA | CAGGGCAAGC | AGGGGCTGC | ATACCTGAGG | 5970 |
| GATGTATCTG | ATGGGCGATT | TGTCCAGCAT | CTCAGCCCAC | ACGCTGAGGT | CTGGCAGGCA | 6030 |
| GTCACTGCTG | AAAGGAAAGC | CAGCCTCCAC | CACGCACCTG | CAAGACACCG | AGCTGTTGCA | 6090 |
| GCCCCAGGAA | | | | | | 6100 |

( 2 ) INFORMATION FOR SEQ ID NO:7:

( i ) SEQUENCE CHARACTERISTICS:
        ( A ) LENGTH: 2262 base pairs
        ( B ) TYPE: nucleic acid
        ( C ) STRANDEDNESS: single
        ( D ) TOPOLOGY: linear ( i i ) MOLECULE TYPE: cDNA to mRNA
        ( A ) DESCRIPTION: Identical to sequence ID NO: 1: with 5'
        and 3'adaptors added to make a full-length cDNA ( i v ) ANTI-SENSE: no ( v i ) ORIGINAL SOURCE:
        ( A ) ORGANISM: human
        ( D ) DEVELOPMENTAL STAGE: fetal
        ( F ) TISSUE TYPE: liver ( v i i ) IMMEDIATE SOURCE:
        ( A ) LIBRARY: cDNA
        ( B ) CLONE: #33 including 5'and 3'adaptors ( x ) PUBLICATION INFORMATION:
( K ) RELEVANT RESIDUES IN SEQ ID NO: 7: FROM 1 TO 2262

( x i ) SEQUENCE DESCRIPTION: SEQ ID NO:7:

| | | | | | | | | | | | | | | | | |
|---|---|---|---|---|---|---|---|---|---|---|---|---|---|---|---|---|
| AATTCCACC | ATG | GGG | TGG | CTC | CCA | AAT | TCC | GTC | CTG | CTG | CTT | CTG | ACT | | | 48 |
| | Met | Gly | Trp | Leu | Pro | Asn | Ser | Val | Leu | Leu | Leu | Leu | Thr | | | |
| | | | | 5 | | | | | | 10 | | | | | | |
| CAA | TAC | TTA | GGG | GTC | CCT | GGG | CAG | CGC | TCG | CCA | TTG | AAT | GAC | TTC | CAA | 96 |
| Gln | Tyr | Leu | Gly | Val | Pro | Gly | Gln | Arg | Ser | Pro | Leu | Asn | Asp | Phe | Gln | |
| | 15 | | | | 20 | | | | | 25 | | | | | | |
| GTG | CTC | CGG | GGC | ACA | GAG | CTA | CAG | CAC | CTG | CTA | CAT | GCG | GTG | GTG | CCC | 144 |
| Val | Leu | Arg | Gly | Thr | Glu | Leu | Gln | His | Leu | Leu | His | Ala | Val | Val | Pro | |
| 30 | | | | | 35 | | | | 40 | | | | | | 45 | |
| GGG | CCT | TGG | CAG | GAG | GAT | GTG | GCA | GAT | GCT | GAA | GAG | TGT | GCT | GGT | CGC | 192 |
| Gly | Pro | Trp | Gln | Glu | Asp | Val | Ala | Asp | Ala | Glu | Glu | Cys | Ala | Gly | Arg | |
| | | | 50 | | | | | 55 | | | | | 60 | | | |
| TGT | GGG | CCC | TTA | ATG | GAC | TGC | CGG | GCC | TTC | CAC | TAC | AAC | GTG | AGC | AGC | 240 |
| Cys | Gly | Pro | Leu | Met | Asp | Cys | Arg | Ala | Phe | His | Tyr | Asn | Val | Ser | Ser | |
| | | | 65 | | | | 70 | | | | | 75 | | | | |
| CAT | GGT | TGC | CAA | CTG | CTG | CCA | TGG | ACT | CAA | CAC | TCG | CCC | CAC | ACG | AGG | 288 |
| His | Gly | Cys | Gln | Leu | Leu | Pro | Trp | Thr | Gln | His | Ser | Pro | His | Thr | Arg | |
| | | 80 | | | | | 85 | | | | | 90 | | | | |
| CTG | CGG | CGT | TCT | GGG | CGC | TGT | GAC | CTC | TTC | CAG | AAG | AAA | GAC | TAC | GTA | 336 |
| Leu | Arg | Arg | Ser | Gly | Arg | Cys | Asp | Leu | Phe | Gln | Lys | Lys | Asp | Tyr | Val | |
| | 95 | | | | 100 | | | | | 105 | | | | | | |
| CGG | ACC | TGC | ATC | ATG | AAC | AAT | GGG | GTT | GGG | TAC | CGG | GGC | ACC | ATG | GCC | 384 |
| Arg | Thr | Cys | Ile | Met | Asn | Asn | Gly | Val | Gly | Tyr | Arg | Gly | Thr | Met | Ala | |
| 110 | | | | | 115 | | | | 120 | | | | | | 125 | |
| ACG | ACC | GTG | GGT | GGC | CTG | CCC | TGC | CAG | GCT | TGG | AGC | CAC | AAG | TTC | CCG | 432 |
| Thr | Thr | Val | Gly | Gly | Leu | Pro | Cys | Gln | Ala | Trp | Ser | His | Lys | Phe | Pro | |
| | | | | 130 | | | | 135 | | | | | 140 | | | |
| AAT | GAT | CAC | AAG | TAC | ACG | CCC | ACT | CTC | CGG | AAT | GGC | CTG | GAA | GAG | AAC | 480 |
| Asn | Asp | His | Lys | Tyr | Thr | Pro | Thr | Leu | Arg | Asn | Gly | Leu | Glu | Glu | Asn | |
| | | | 145 | | | | 150 | | | | | 155 | | | | |
| TTC | TGC | CGT | AAC | CCT | GAT | GGC | GAC | CCC | GGA | GGT | CCT | TGG | TGC | TAC | ACA | 528 |
| Phe | Cys | Arg | Asn | Pro | Asp | Gly | Asp | Pro | Gly | Gly | Pro | Trp | Cys | Tyr | Thr | |
| | | 160 | | | | | 165 | | | | | 170 | | | | |
| ACA | GAC | CCT | GCT | GTG | CGC | TTC | CAG | AGC | TGC | GGC | ATC | AAA | TCC | TGC | CGG | 576 |
| Thr | Asp | Pro | Ala | Val | Arg | Phe | Gln | Ser | Cys | Gly | Ile | Lys | Ser | Cys | Arg | |
| | 175 | | | | | 180 | | | | | 185 | | | | | |
| GAG | GCC | GCG | TGT | GTC | TGG | TGC | AAT | GGC | GAG | GAA | TAC | CGC | GGC | GCG | GTA | 624 |
| Glu | Ala | Ala | Cys | Val | Trp | Cys | Asn | Gly | Glu | Glu | Tyr | Arg | Gly | Ala | Val | |
| 190 | | | | | 195 | | | | 200 | | | | | | 205 | |
| GAC | CGC | ACG | GAG | TCA | GGG | CGC | GAG | TGC | CAG | CGC | TGG | GAT | CTT | CAG | CAC | 672 |
| Asp | Arg | Thr | Glu | Ser | Gly | Arg | Glu | Cys | Gln | Arg | Trp | Asp | Leu | Gln | His | |
| | | | | 210 | | | | 215 | | | | | 220 | | | |
| CCG | CAC | CAG | CAC | CCC | TTC | GAG | CCG | GGC | AAG | TTC | CTC | GAC | CAA | GGT | CTG | 720 |
| Pro | His | Gln | His | Pro | Phe | Glu | Pro | Gly | Lys | Phe | Leu | Asp | Gln | Gly | Leu | |
| | | | 225 | | | | 230 | | | | | 235 | | | | |
| GAC | GAC | AAC | TAT | TGC | CGG | AAT | CCT | GAC | GGC | TCC | GAG | CGG | CCA | TGG | TGC | 768 |
| Asp | Asp | Asn | Tyr | Cys | Arg | Asn | Pro | Asp | Gly | Ser | Glu | Arg | Pro | Trp | Cys | |
| | | 240 | | | | | 245 | | | | | 250 | | | | |
| TAC | ACT | ACG | GAT | CCG | CAG | ATC | GAG | CGA | GAG | TTC | TGT | GAC | CTC | CCC | CGC | 816 |
| Tyr | Thr | Thr | Asp | Pro | Gln | Ile | Glu | Arg | Glu | Phe | Cys | Asp | Leu | Pro | Arg | |
| | 255 | | | | | 260 | | | | | 265 | | | | | |
| TGC | GGG | TCC | GAG | GCA | CAG | CCC | CGC | CAA | GAG | GCC | ACA | ACT | GTC | AGC | TGC | 864 |
| Cys | Gly | Ser | Glu | Ala | Gln | Pro | Arg | Gln | Glu | Ala | Thr | Thr | Val | Ser | Cys | |
| 270 | | | | | 275 | | | | | 280 | | | | | 285 | |
| TTC | CGC | GGG | AAG | GGT | GAG | GGC | TAC | CGG | GGC | ACA | GCC | AAT | ACC | ACC | ACT | 912 |
| Phe | Arg | Gly | Lys | Gly | Glu | Gly | Tyr | Arg | Gly | Thr | Ala | Asn | Thr | Thr | Thr | |
| | | | | 290 | | | | | 295 | | | | | 300 | | |

| | | | | | | | | | | | | | | | | |
|---|---|---|---|---|---|---|---|---|---|---|---|---|---|---|---|---|
| GCG | GGC | GTA | CCT | TGC | CAG | CGT | TGG | GAC | GCG | CAA | ATC | CCT | CAT | CAG | CAC | 960 |
| Ala | Gly | Val | Pro | Cys | Gln | Arg | Trp | Asp | Ala | Gln | Ile | Pro | His | Gln | His | |
| | | | 305 | | | | 310 | | | | | | 315 | | | |
| CGA | TTT | ACG | CCA | GAA | AAA | TAC | GCG | TGC | AAA | GAC | CTT | CGG | GAG | AAC | TTC | 1008 |
| Arg | Phe | Thr | Pro | Glu | Lys | Tyr | Ala | Cys | Lys | Asp | Leu | Arg | Glu | Asn | Phe | |
| | | 320 | | | | | 325 | | | | | 330 | | | | |
| TGC | CGG | AAC | CCC | GAC | GGC | TCA | GAG | GCG | CCC | TGG | TGC | TTC | ACA | CTG | CGG | 1056 |
| Cys | Arg | Asn | Pro | Asp | Gly | Ser | Glu | Ala | Pro | Trp | Cys | Phe | Thr | Leu | Arg | |
| | 335 | | | | | 340 | | | | | 345 | | | | | |
| CCC | GGC | ATG | CGC | GCG | GCC | TTT | TGC | TAC | CAG | ATC | CGG | CGT | TGT | ACA | GAC | 1104 |
| Pro | Gly | Met | Arg | Ala | Ala | Phe | Cys | Tyr | Gln | Ile | Arg | Arg | Cys | Thr | Asp | |
| 350 | | | | | 355 | | | | | 360 | | | | | 365 | |
| GAC | GTG | CGG | CCC | CAG | GAC | TGC | TAC | CAC | GGC | GCA | GGG | GAG | CAG | TAC | CGC | 1152 |
| Asp | Val | Arg | Pro | Gln | Asp | Cys | Tyr | His | Gly | Ala | Gly | Glu | Gln | Tyr | Arg | |
| | | | | 370 | | | | | 375 | | | | | 380 | | |
| GGC | ACG | GTC | AGC | AAG | ACC | CGC | AAG | GGT | GTC | CAG | TGC | CAG | CGC | TGG | TCC | 1200 |
| Gly | Thr | Val | Ser | Lys | Thr | Arg | Lys | Gly | Val | Gln | Cys | Gln | Arg | Trp | Ser | |
| | | | 385 | | | | | 390 | | | | | 395 | | | |
| GCT | GAG | ACG | CCG | CAC | AAG | CCG | CAG | TTC | ACG | TTT | ACC | TCC | GAA | CCG | CAT | 1248 |
| Ala | Glu | Thr | Pro | His | Lys | Pro | Gln | Phe | Thr | Phe | Thr | Ser | Glu | Pro | His | |
| | | | 400 | | | | | 405 | | | | | 410 | | | |
| GCA | CAA | CTG | GAG | GAG | AAC | TTC | TGC | CGG | AAC | CCA | GAT | GGG | GAT | AGC | CAT | 1296 |
| Ala | Gln | Leu | Glu | Glu | Asn | Phe | Cys | Arg | Asn | Pro | Asp | Gly | Asp | Ser | His | |
| | 415 | | | | | 420 | | | | | 425 | | | | | |
| GGG | CCC | TGG | TGC | TAC | ACG | ATG | GAC | CCA | AGG | ACC | CCA | TTC | GAC | TAC | TGT | 1344 |
| Gly | Pro | Trp | Cys | Tyr | Thr | Met | Asp | Pro | Arg | Thr | Pro | Phe | Asp | Tyr | Cys | |
| 430 | | | | | 435 | | | | | 440 | | | | | 445 | |
| GCC | CTG | CGA | CGC | TGC | GCT | GAT | GAC | CAG | CCG | CCA | TCA | ATC | CTG | GAC | CCC | 1392 |
| Ala | Leu | Arg | Arg | Cys | Ala | Asp | Asp | Gln | Pro | Pro | Ser | Ile | Leu | Asp | Pro | |
| | | | | 450 | | | | | 455 | | | | | 460 | | |
| CCA | GAC | CAG | GTG | CAG | TTT | GAG | AAG | TGT | GGC | AAG | AGG | GTG | GAT | CGG | CTG | 1440 |
| Pro | Asp | Gln | Val | Gln | Phe | Glu | Lys | Cys | Gly | Lys | Arg | Val | Asp | Arg | Leu | |
| | | | 465 | | | | | 470 | | | | | 475 | | | |
| GAT | CAG | CGG | CGT | TCC | AAG | CTG | CGC | GTG | GTT | GGG | GGC | CAT | CCG | GGC | AAC | 1488 |
| Asp | Gln | Arg | Arg | Ser | Lys | Leu | Arg | Val | Val | Gly | Gly | His | Pro | Gly | Asn | |
| | | | 480 | | | | | 485 | | | | | 490 | | | |
| TCA | CCC | TGG | ACA | GTC | AGC | TTG | CGG | AAT | CGG | CAG | GGC | CAG | CAT | TTC | TGC | 1536 |
| Ser | Pro | Trp | Thr | Val | Ser | Leu | Arg | Asn | Arg | Gln | Gly | Gln | His | Phe | Cys | |
| | 495 | | | | | 500 | | | | | 505 | | | | | |
| GGG | GGG | TCT | CTA | GTG | AAG | GAG | CAG | TGG | ATA | CTG | ACT | GCC | CGG | CAG | TGC | 1584 |
| Gly | Gly | Ser | Leu | Val | Lys | Glu | Gln | Trp | Ile | Leu | Thr | Ala | Arg | Gln | Cys | |
| 510 | | | | | 515 | | | | | 520 | | | | | 525 | |
| TTC | TCC | TCC | TGC | CAT | ATG | CCT | CTC | ACG | GGC | TAT | GAG | GTA | TGG | TTG | GGC | 1632 |
| Phe | Ser | Ser | Cys | His | Met | Pro | Leu | Thr | Gly | Tyr | Glu | Val | Trp | Leu | Gly | |
| | | | | 530 | | | | | 535 | | | | | 540 | | |
| ACC | CTG | TTC | CAG | AAC | CCA | CAG | CAT | GGA | GAG | CCA | AGC | CTA | CAG | CGG | GTC | 1680 |
| Thr | Leu | Phe | Gln | Asn | Pro | Gln | His | Gly | Glu | Pro | Ser | Leu | Gln | Arg | Val | |
| | | | 545 | | | | | 550 | | | | | 555 | | | |
| CCA | GTA | GCC | AAG | ATG | GTG | TGT | GGG | CCC | TCA | GGC | TCC | CAG | CTT | GTC | CTG | 1728 |
| Pro | Val | Ala | Lys | Met | Val | Cys | Gly | Pro | Ser | Gly | Ser | Gln | Leu | Val | Leu | |
| | | | 560 | | | | | 565 | | | | | 570 | | | |
| CTC | AAG | CTG | GAG | AGA | TCT | GTG | ACC | CTG | AAC | CAG | CGC | GTG | GCC | CTG | ATC | 1776 |
| Leu | Lys | Leu | Glu | Arg | Ser | Val | Thr | Leu | Asn | Gln | Arg | Val | Ala | Leu | Ile | |
| | 575 | | | | | 580 | | | | | 585 | | | | | |
| TGC | CTG | CCC | CCT | GAA | TGG | TAT | GTG | GTG | CCT | CCA | GGG | ACC | AAG | TGT | GAG | 1824 |
| Cys | Leu | Pro | Pro | Glu | Trp | Tyr | Val | Val | Pro | Pro | Gly | Thr | Lys | Cys | Glu | |
| 590 | | | | | 595 | | | | | 600 | | | | | 605 | |
| ATT | GCA | GGC | TGG | GGT | GAG | ACC | AAA | GGT | ACG | GGT | AAT | GAC | ACA | GTC | CTA | 1872 |
| Ile | Ala | Gly | Trp | Gly | Glu | Thr | Lys | Gly | Thr | Gly | Asn | Asp | Thr | Val | Leu | |
| | | | | 610 | | | | | 615 | | | | | 620 | | |

```
AAT GTG GCC TTG CTG AAT GTC ATC TCC AAC CAG GAG TGT AAC ATC AAG        1920
Asn Val Ala Leu Leu Asn Val Ile Ser Asn Gln Glu Cys Asn Ile Lys
            625                 630                 635

CAC CGA GGA CGT GTG CGT GAG AGT GAG ATG TGC ACT GAG GGA CTG TTG        1968
His Arg Gly Arg Val Arg Glu Ser Glu Met Cys Thr Glu Gly Leu Leu
            640                 645                 650

GCC CCT GTG GGG GCC TGT GAG GGT GAC TAC GGG GGC CCA CTT GCC TGC        2016
Ala Pro Val Gly Ala Cys Glu Gly Asp Tyr Gly Gly Pro Leu Ala Cys
            655                 660                 665

TTT ACC CAC AAC TGC TGG GTC CTG GAA GGA ATT ATA ATC CCC AAC CGA        2064
Phe Thr His Asn Cys Trp Val Leu Glu Gly Ile Ile Ile Pro Asn Arg
670                 675                 680                 685

GTA TGC GCA AGG TCC CGC TGG CCA GCT GTC TTC ACG CGT GTC TCT GTG        2112
Val Cys Ala Arg Ser Arg Trp Pro Ala Val Phe Thr Arg Val Ser Val
            690                 695                 700

TTT GTG GAC TGG ATT CAC AAG GTC ATG AGA CTG GGT TAGGCCCAGC             2158
Phe Val Asp Trp Ile His Lys Val Met Arg Leu Gly
            705                 710

CTTGATGCCA TATGCCTTGG GGAGGACAAA ACTTCTTGTC AGACATAAAG CCATGTTTCC      2218

TCTTTATGCC TGTAAAAAAA AAAAAAAAGA ACGCCCATG GTGG                        2262
```

(2) INFORMATION FOR SEQ ID NO:8:

(i) SEQUENCE CHARACTERISTICS:
        (A) LENGTH: 711 amino acids
        (B) TYPE: amino acid
        (D) TOPOLOGY: linear (ii) MOLECULE TYPE: protein (ix) FEATURE:
        (A) NAME/KEY: signal sequence
        (B) LOCATION: 1 to 31
        (C) IDENTIFICATION METHOD: similarity to other signal
            sequences; hydrophobic; numbered 1 to 31 since we do
            not if the actual signal peptidase site is after amino
            acid 31 or not; this has not been determined
            experimentally. We do know that the protein is secreted.
        (D) OTHER INFORMATION: This sequence has a polymorphism
            at amino acid 13; a Cys is shown here, the other amino
            acid is Tyr.

(x) PUBLICATION INFORMATION:
        (A) AUTHORS: Han, Su, Stuart, Lorie A., Degen, Sandra J.
            Friezner
        (B) TITLE: Characterization of the DNF15S2 locus on human
            chromosome 3: Identification of a gene coding for four
            kringle domains with homology to hepatocyte growth factor
        (C) JOURNAL: Biochemistry
        (D) VOLUME: 30
        (E) ISSUE: 40
        (F) PAGES: 9768-9780
        (G) DATE: 8 October 1991
        (K) RELEVANT RESIDUES IN SEQ ID NO: 8: FROM 1 TO 711

(xi) SEQUENCE DESCRIPTION: SEQ ID NO: 8:

```
Met Gly Trp Leu Pro Leu Leu Leu Leu Leu Thr Gln Cys Leu Gly Val
                5                   10                  15

Pro Gly Gln Arg Ser Pro Leu Asn Asp Phe Gln Val Leu Arg Gly Thr
            20                  25                  30

Glu Leu Gln His Leu Leu His Ala Val Val Pro Gly Pro Trp Gln Glu
            35                  40                  45

Asp Val Ala Asp Ala Glu Glu Cys Ala Gly Arg Cys Gly Pro Leu Met
            50                  55                  60

Asp Cys Arg Ala Phe His Tyr Asn Val Ser Ser His Gly Cys Gln Leu
65                  70                  75                  80
```

```
Leu Pro Trp Thr Gln His Ser Pro His Thr Arg Leu Arg Arg Ser Gly
                85                  90                    95

Arg Cys Asp Leu Phe Gln Lys Lys Asp Tyr Val Arg Thr Cys Ile Met
            100             105                 110

Asn Asn Gly Val Gly Tyr Arg Gly Thr Met Ala Thr Thr Val Gly Gly
        115             120                 125

Leu Pro Cys Gln Ala Trp Ser His Lys Phe Pro Asn Asp His Lys Tyr
    130             135                 140

Thr Pro Thr Leu Arg Asn Gly Leu Glu Glu Asn Phe Cys Arg Asn Pro
145             150              155                         160

Asp Gly Asp Pro Gly Gly Pro Trp Cys Tyr Thr Thr Asp Pro Ala Val
            165             170                 175

Arg Phe Gln Ser Cys Gly Ile Lys Ser Cys Arg Glu Ala Ala Cys Val
            180             185                 190

Trp Cys Asn Gly Glu Glu Tyr Arg Gly Ala Val Asp Arg Thr Glu Ser
        195             200                 205

Gly Arg Glu Cys Gln Arg Trp Asp Leu Gln His Pro His Gln His Pro
    210             215                 220

Phe Glu Pro Gly Lys Phe Leu Asp Gln Gly Leu Asp Asp Asn Tyr Cys
225             230                 235                     240

Arg Asn Pro Asp Gly Ser Glu Arg Pro Trp Cys Tyr Thr Thr Asp Pro
            245             250                 255

Gln Ile Glu Arg Glu Phe Cys Asp Leu Pro Arg Cys Gly Ser Glu Ala
            260             265                 270

Gln Pro Arg Gln Glu Ala Thr Thr Val Ser Cys Phe Arg Gly Lys Gly
        275             280                 285

Glu Gly Tyr Arg Gly Thr Ala Asn Thr Thr Thr Ala Gly Val Pro Cys
    290             295                 300

Gln Arg Trp Asp Ala Gln Ile Pro His Gln His Arg Phe Thr Pro Glu
305             310                 315                     320

Lys Tyr Ala Cys Lys Asp Leu Arg Glu Asn Phe Cys Arg Asn Pro Asp
            325             330                 335

Gly Ser Glu Ala Pro Trp Cys Phe Thr Leu Arg Pro Gly Met Arg Ala
        340             345                 350

Ala Phe Cys Tyr Gln Ile Arg Arg Cys Thr Asp Asp Val Arg Pro Gln
        355             360                 365

Asp Cys Tyr His Gly Ala Gly Glu Gln Tyr Arg Gly Thr Val Ser Lys
    370             375                 380

Thr Arg Lys Gly Val Gln Cys Gln Arg Trp Ser Ala Glu Thr Pro His
385             390                 395                     400

Lys Pro Gln Phe Thr Phe Thr Ser Glu Pro His Ala Gln Leu Glu Glu
            405             410                 415

Asn Phe Cys Arg Asn Pro Asp Gly Asp Ser His Gly Pro Trp Cys Tyr
        420             425                 430

Thr Met Asp Pro Arg Thr Pro Phe Asp Tyr Cys Ala Leu Arg Arg Cys
        435             440                 445

Ala Asp Asp Gln Pro Pro Ser Ile Leu Asp Pro Pro Asp Gln Val Gln
    450             455                 460

Phe Glu Lys Cys Gly Lys Arg Val Asp Arg Leu Asp Gln Arg Arg Ser
465             470                 475                     480

Lys Leu Arg Val Val Gly Gly His Pro Gly Asn Ser Pro Trp Thr Val
            485             490                 495

Ser Leu Arg Asn Arg Gln Gly Gln His Phe Cys Gly Gly Ser Leu Val
```

|     |     |     |     |     | 500 |     |     |     |     | 505 |     |     |     |     | 510 |     |     |
|-----|-----|-----|-----|-----|-----|-----|-----|-----|-----|-----|-----|-----|-----|-----|-----|-----|-----|
| Lys | Glu | Gln | Trp | Ile | Leu | Thr | Ala | Arg | Gln | Cys | Phe | Ser | Ser | Cys | His |
|     |     | 515 |     |     |     |     | 520 |     |     |     |     | 525 |     |     |     |

Met Pro Leu Thr Gly Tyr Glu Val Trp Leu Gly Thr Leu Phe Gln Asn
530                535                540

Pro Gln His Gly Glu Pro Ser Leu Gln Arg Val Pro Val Ala Lys Met
545             550                555                560

Val Cys Gly Pro Ser Gly Ser Gln Leu Val Leu Leu Lys Leu Glu Arg
565                570                575

Ser Val Thr Leu Asn Gln Arg Val Ala Leu Ile Cys Leu Pro Pro Glu
580                585                590

Trp Tyr Val Val Pro Pro Gly Thr Lys Cys Glu Ile Ala Gly Trp Gly
595                600                605

Glu Thr Lys Gly Thr Gly Asn Asp Thr Val Leu Asn Val Ala Leu Leu
610                615                620

Asn Val Ile Ser Asn Gln Glu Cys Asn Ile Lys His Arg Gly Arg Val
625                630                635                640

Arg Glu Ser Glu Met Cys Thr Glu Gly Leu Leu Ala Pro Val Gly Ala
645                650                655

Cys Glu Gly Asp Tyr Gly Gly Pro Leu Ala Cys Phe Thr His Asn Cys
660                665                670

Trp Val Leu Glu Gly Ile Ile Ile Pro Asn Arg Val Cys Ala Arg Ser
675                680                685

Arg Trp Pro Ala Val Phe Thr Arg Val Ser Val Phe Val Asp Trp Ile
690                695                700

His Lys Val Met Arg Leu Gly
705                710

( 2 ) INFORMATION FOR SEQ ID NO:9:

( i ) SEQUENCE CHARACTERISTICS:
        ( A ) LENGTH: 27 bases
        ( B ) TYPE: nucleic acid
        ( C ) STRANDEDNESS: single
        ( D ) TOPOLOGY: linear ( i i ) MOLECULE TYPE: cDNA to mRNA
        ( A ) DESCRIPTION: This is an oligonucleotide used
            with SEQ ID NO:10 to form a 5'end adaptor to
            construct the cDNA in SEQ ID NO:7

( i v ) ANTI-SENSE: no ( x ) PUBLICATION INFORMATION:
        ( K ) RELEVANT RESIDUES IN SEQ ID NO: 1: FROM 1 TO 27

( x i ) SEQUENCE DESCRIPTION: SEQ ID NO:9:

GCGAATTCCA CCATGGGGTG GCTCCCA                                                                    27

( 2 ) INFORMATION FOR SEQ ID NO:10:

( i ) SEQUENCE CHARACTERISTICS:
        ( A ) LENGTH: 31 bases
        ( B ) TYPE: nucleic acid
        ( C ) STRANDEDNESS: single
        ( D ) TOPOLOGY: linear ( i i ) MOLECULE TYPE: cDNA to mRNA
        ( D ) DESCRIPTION: This is an oligonucleotide used
            with SEQ ID NO:9 to form a 5'end adaptor to
            construct the cDNA in SEQ ID NO:7

( i v ) ANTI-SENSE: yes ( x ) PUBLICATION INFORMATION:
( K ) RELEVANT RESIDUES IN SEQ ID NO: 1: FROM 1 TO 31

( x i ) SEQUENCE DESCRIPTION: SEQ ID NO:10:

AATTTGGGAG CCACCCCATG GTGGAATTCG C  31

GENE FOR A GROWTH FACTOR AND ITS CDNA AND PROTEIN

This is a continuation of U.S. Ser. No. 07/882,925, filed May 14, 1992, now U.S. Pat. No. 5,315,000.

BACKGROUND

Growth factors are important for normal developmental processes, as well as for healing of wounds. Their abnormal expression has been implicated in neoplasia and other proliferative disorders. The kringle-containing protein hepatocyte growth factor (HGF) was originally identified as a potent growth factor involved in liver regeneration after liver injury or partial hepatectomy. It is now known that HGF functions as a growth factor for a broad spectrum of tissues and cell types. In addition, it has been recently discovered that HGF is identical to scatter factor (SF) a cytokine secreted from certain fibroblasts that enhances movement and causes the dissociation and scattering of epithelial cells (Gheradi & Stoker, 1990). The proto-oncogene c-met, a tyrosine kinase, has been found to be the cell surface receptor for HGF (Rubin et al., 1991; Bottaro et al., 1991). These properties may be important for metastasis of tumor cells.

In 1973 it was recognized that serum from partially hepatectomized rats stimulated hepatocyte proliferation in vitro (Morley et al., 1973). One of the agents responsible for this phenomenon was identified and isolated from such serum and from serum of patients with fulminant liver failure (Morley et al., 1973; Michalopoulous et al., 1984; Nakamura et al., 1984; Gohda et al., 1988). This agent was named hepatopoietin A or hepatocyte growth factor (HGF). HGF stimulates hepatocyte DNA synthesis and proliferation. Its serum concentration increases dramatically after rats undergo partial hepatectomy and decreases when the liver regenerates. HGF is produced by non-parenchymal liver cells (Schirmacher et al., 1992) and acts directly on hepatocytes in a paracrine fashion to stimulate cell multiplication. Although HGF stimulates growth of normal hepatocytes, it also has antiproliferative effects on hepatocarcinoma cells in culture (Tajima et al., 1991; Shiota et al., 1992).

HGF is a heterodimer of 82 kD composed of a α- and β-subunit with 51 kD and 26 kD molecular weight, respectively. The cDNAs for human and rat HGF have been cloned and characterized by several groups (Miyazawa et al., 1989; Nakamura et al., 1989; Okajima et al., 1990; Seki et al., 1990; Tashiro et al., 1990; Rubin et al., 1991).

HGF has no obvious homology with other known growth factors but is 38% homologous to plasminogen. It contains four kringle domains followed by a serine protease-like domain where the active site His and Ser have been changed to Gln and Tyr, respectively. HGF has no detectable protease activity. At present the function of the kringle domains in HGF is unknown.

Kringle domains were first identified in bovine prothrombin as an internal duplication of a triple-disulfide-bonded structure containing approximately 80 amino acids (Magnusson et al., 1975). Kringle domains were until recently only characterized in plasma proteins that functioned in blood coagulation or fibrinolysis (Davie et al., 1986) which includes prothrombin, Factor XII, urokinase-type plasminogen activator, tissue-type plasminogen activator and plasminogen. Recently, apolipoprotein(a) and HGF have also been shown to contain kringle domains. Apolipoprotein(a) is thought to be involved in atherosclerosis (McLean et al., 1987). Kringle structures are thought to function autonomously (Trexler & Patthy, 1983; van Zonneveld et al., 1986) and fold independently (Tulinsky et al., 1988).

Kringles appear to be protein-binding domains and have been shown to be essential for the function of prothrombin, plasminogen and tissue plasminogen activator. The functions of all other kringle structures has not been determined, but since these structures are over 50% identical with each other, it is reasonable to assume that they are involved in binding interactions with other proteins essential for their regulation.

Two functional variants of HGF have been identified and have been found to be expressed at variable levels depending on the cell line or tissue being analyzed. A form of HGF containing the amino-terminal end of the protein including the first two kringle domains appears to result from alternative processing of the gene coding for HGF (Chan et al., 1991; Miyazawa et al., 1991). This variant binds to the c-met receptor although not as effectively as the full-length protein. Another variant has a five amino acid deletion in the first kringle domain that appears to have no effect on its activity (Seki et al., 1990; Rubin et al., 1991). Specific domains in HGF have been deleted by using techniques in molecular biology and the resultant proteins have been studied in various assays where native HGF can be measured. Matsumoto et al. (1991) concluded that the amino-terminal portion of the protein including the first and second kringle domains are essential for biological activity of HGF and possibly binding to the receptor.

Chromosomal abnormalities in a number of neoplastic diseases are sometimes associated with the activation of a proto-oncogene or the loss of a gene that suppresses tumor growth. Growth factors are important for normal developmental processes, as well as healing of wounds. Their abnormal expression has been implicated in neoplasia and other proliferative disorders (Aaronson, 1991). Growth factors are involved in signaling pathways that influence normal cellular differentiation. These proteins cause cells in the resting phase (Go) to enter and progress through the cell cycle. oncogenic mutations in several growth factors result in unregulated cell growth. Tumor suppressor genes are genes expressed in normal cells that play regulatory roles in cell proliferation, differentiation and other cellular events. Loss or inactivation of these genes is oncogenic. Tumor suppressor genes that have been extensively characterized include the genes for colon carcinoma, retinoblastoma, type 2 neurofibromatosis, the genes involved in Wilms tumor and the p53 gene (reviewed in Weinberg, 1991). Tumor suppressor genes are involved in cell cycle control, signal transduction, angiogenesis, and development (Sager, 1989; Weinberg, 1991).

The concept that the loss of genetic material or the inactivation of a gene plays an important role in human cancer is based on the original observation that somatic cell hybrids between tumor cells and normal cells were no longer tumorigenic. This indicated that normal cells contain genes coding for tumor suppressors whose function was absent in cancer cells. In addition, cytogenic and restriction fragment length polymorphism (RFLP) analyses have established an association between the loss of genetic material on specific chromosomes and the development of various human malignancies.

Deletion of the short arm of human chromosome 3 has been implicated in small cell lung carcinoma (SCLC; Whang-Peng et al., 1982; Naylor et al., 1987), other lung cancers (Kok et al., 1987; Brauch et al., 1987), renal cell carcinoma (Zbar et al., 1987; Kovacs et al., 1988) and yon Hippel-Lindau syndrome (Seizinger et al., 1988) which suggests that one or more tumor suppressor genes reside on chromosome 3p which manifest their transformed phenotype upon their inactivation. The chromosomal locus DNF15S2 (also called D3F15S2) is a RFLP probe that most consistently is associated with loss of heterozygosity in SCLC, being detected in virtually 100% of SCLC.

Lung cancer is a common human malignancy with 150,000 new cases reported each year in the United States. Unfortunately, 90% of affected persons will die within 5 years of diagnosis. Mortality due to lung cancer has increased more than 15% since 1973. Increases in cigarette smoking from 1900 until the early 1960s has transformed lung cancer from a rare disease at the turn of the century to the current leading cause of cancer death. In women, lung cancer surpassed breast cancer as the leading cause of cancer death in 1986 with rates expected to continue to increase for at least another ten years (Henderson et al., 1991).

Lung cancer is divided into small cell and non-small cell varieties. The non-small cell lung cancers include adenocarcinoma, squamous and epidermoid lung cancer and large-cell lung cancer. Chromosome 3p(14–23) changes have been found in nearly all small cell lung cancers and in a large fraction of non-small cell lung cancers.

Cancer of the kidney accounts for 1–2% of all malignancies (excluding skin cancer) with renal cell carcinoma comprising 85% of these. Renal cell carcinoma (RCC) occurs in sporadic and familial forms and are commonly seen in the age group between 50 to 70 years. Cigarette smoking is a known risk factor for this form of cancer (Walter et al., 1989). Deletion of the short arm of chromosome 3 is the most commonly involved region of the genome in RCC and therefore appears to play a role in the development and/or progression of this form of cancer.

Several genes have been localized near or at the D3F15S2 locus. The ERβEAB locus coding for a DNA-binding thyroid hormone receptor is localized to human chromosome 3p21–25, and overlaps deletions found in SCLC. Leduc et al. (1989) determined that many non-SCLC tumors retained both ERBAB alleles while the D3F15S2 locus was reduced to homozygosity, ruling out a role for the thyroid hormone receptor in this form of cancer. The gene encoding aminoacylase-1 at 3p21 is inactivated in a large fraction of SCLC (Naylor et al., 1982, 1989). A similar allelic loss is observed in sporadic renal cancers and there are cytogenetic abnormalities of this region in familial renal cell cancer. The gene coding for protein-tyrosine phosphatase$\gamma$ (PTP$\gamma$) maps to 3p21 (LaForgia et al., 1991). This protein and homologous family members reverse the effect of protein tyrosine kinases, of which, some have been identified as oncogenes (ie., met, fms, kit, ERBB). In one study, one PTP$\gamma$ allele was deleted in 3 of 5 renal carcinoma cell lines and in 5 of 10 lung carcinoma samples tested (LaForgia et al., 1991). In summary, the key gene(s) responsible for tumor suppressor activity at this locus is unknown, although there are some candidate genes.

SUMMARY OF THE INVENTION

The present invention is based on the isolation and characterization of the human gene located at the D3F15S2 locus on human chromosome 3 referred to as L5/3. The protein coded for by this gene is referred to as the L5/3 protein. The translated amino acid sequence indicates that L5/3 protein is composed of four kringle structures followed by a serine protease-like domain. This is identical in composition to hepatocyte growth factor (HGF) although L5/3 protein and HGF are only 50% identical to each other when their amino acid sequences are compared. The corresponding human cDNA has also been isolated, as well as the mouse gene and cDNA.

The L5/3 protein can be employed to alter cell growth (as a growth factor or tumor suppressor). The L5/3 protein has properties similar to HGF that is actively involved in liver regeneration.

In addition, the L5/3 gene is identical to the gene at a locus on human chromosome 3 (3p21) that is deleted in DNA from all small cell lung carcinomas and has been hypothesized to contain one or more tumor suppressor genes. Thus this isolated gene L5/3 can be used as a probe to provide an indication of a predisposition for certain cancers. Further, identification of the coded L5/3 protein can also be utilized to evaluate a predisposition to cancer.

BRIEF DESCRIPTION OF THE DRAWINGS

The FIGURE is a schematic diagram of the amino acid sequence of human L5/3, SEQ ID NO:8.

DETAILED DESCRIPTION OF THE INVENTION

The methods discussed below to obtain DNA sequences encoding L5/3 are merely for purposes of illustration and are typical of those that might be used. However, other procedures may also be employed.

The human L5/3 gene was isolated using a multistep process employing various DNA and cDNA probes which were both of human and mouse origin. Further, the initial probe is a bovine prothrombin cDNA.

A human liver genomic DNA library cloned into bacteriophage Charon 28 (Lawn et al., 1978) was obtained from Dr. Tom Maniatis, Harvard University (this library is presently available from the ATCC). This library is an Alu/Hae III fetal human genomic DNA library. The library containing approximately $2 \times 10^6$ recombinant phage was plated out on E. coli strain LE392 and grown overnight at 37° C. and was screened by the in situ plaque hybridization technique of Benton & Davis (1977) as modified by Woo (1979).

Approximately $1 \times 10^8$ cpm of nick-translated bovine prothrombin cDNA probe (obtained by Ava I and Bam HI digestion of pBII102; this probe is 1200 bp in length coding for amino acids 109–500; MacGillivray & Davie, 1984) was hybridized to nitrocellulose filters containing the recombinant phage under conditions of reduced stringency. These conditions included hybridization at 60° overnight in 2×Denhardt's solution (0.04% polyvinylpyrrolidone, 0.04% Ficoll and 0.04% bovine serum albumin) containing 6×SSC [1×SSC: 0.15M sodium chloride and 0.015M trisodium citrate (pH 7.0)], 1 mM EDTA and 0.5% sodium dodecyl sulfate (SDS). The filters were washed three times at 60° C. in 6×SSC with 0.5% SDS. Twelve positive phage were identified. Two of these phage have been identified to code for the human L5 gene.

This human L5 gene and its method of selection is also disclosed in the doctoral thesis of Sandra J. Friezner Degen entitled *Isolation* and *Characterization of the Human Prothrombin Gene And Related Genes* published in 1982. As discussed below this gene characterized as L5 is an incomplete gene but is useful in isolation and characterization of the gene of the present invention. Until now its function was also unknown.

The obtained L5 gene was then used to obtain the corresponding human L5 cDNA. The human cDNA corresponding to the L5 gene was used to obtain the mouse cDNA. This mouse cDNA was in turn used to obtain the mouse L5/3 gene. The mouse L5/3 gene was used to obtain the human L5/3 gene.

A λgt11 cDNA library prepared from human fetal liver mRNA (provided by Dr. Vincent Kidd, University of Alabama, Birmingham; Kwok et al., 1985) was screened for the human cDNA coding for L5 by using a probe isolated from the human L5 gene (680 bp Bam HI and Hind III fragment isolated from a 1850 bp subclone (obtained by digestion of L5 with Hind III and cloning into pBR322) and coding for part of the second kringle and all of the third; nucleotides 2190–2868 of Sequence ID No. 6). Approximately $1 \times 10^5$ phage were screened at high stringency using standard techniques (Degen & Davie, 1987). These conditions include hybridization with the same solution used for isolation of the human L5 gene discussed above but at 68° C. and washing at 68° C. in 1×SSC containing 0.5% SDS. Six positives were identified. The longest (#46) was 1.9 kb in length. A 5'-end fragment from this cDNA (340 bp Eco RI and Nco I fragment coding for part of kringles 1 and 2; nucleotides 388–733 in sequence ID No. 1) was used to rescreen the library to obtain clones with longer 5' ends. Two clones (#33 and #19) were identified and characterized (Sequence ID No. 1,2,3). The longest clone (#33) is 2200 bp in length excluding the poly(A) tail and is not full-length since its 5' end starts 16 bp downstream from the putative initiator methionine codon in the first exon of the gene (starting at nucleotide 290 in Sequence ID No. 6).

A γgt10 mouse liver cDNA library (Stratagene, La Jolla, Calif.; from mouse strain C57BL/6) was then screened using a fragment from the human cDNA #33. Approximately $1 \times 10^6$ phage were screened with a probe isolated from the 5' end of the human cDNA (the 340 bp fragment was isolated from human cDNA-33 after digestion with Eco RI and Kpn I and coded for the amino-terminal portion of the protein including eight amino acids of the first kringle; nucleotides 1 to 334 in Sequence ID No. 1) using the conditions of reduced stringency discussed above for the isolation of the human L5 gene. These conditions were used to allow for cross species hybridization. Ten positives were identified and eight were characterized after cloning the cDNAs into pBR322.

The longest cDNA (pML5-2) was 2188 bp in length and was not full-length since the open reading frame was present at the 5' end of the sequence with no codon for the initiator methionine in-frame with the coding sequence (Sequence ID No. 4). After determination of the sequence of the mouse gene it was determined that the cDNA lacked 44 bp of coding and 94 bp of 5' noncoding sequence at its 5' end.

A mouse liver genomic DNA library cloned into the Bam HI site of EMBL-3 SP6/T7 (Clontech; mouse strain Balb/c; catalog #M 1030 J) was screened for the gene coding for mouse L5/3. Approximately $1 \times 10^6$ phage from the library were screened with a probe isolated from the previously isolated mouse cDNA (the 1450 bp insert was isolated from pML5-2 after digestion with Eco RI and coded for eight amino acids of the second kringle, all of the third and fourth kringles and the serine protease-like domain; nucleotides 738 to 2188 in sequence ID No. 4) using the identical high stringency conditions discussed above for the isolation of the human L5 cDNA. On the initial screen, 65 positives were identified; 9 were characterized. Restriction fragments of phage DNA were subcloned into pBR322.

A second human genomic DNA library prepared from placental DNA using EMBL-3 SP6/T7 as the cloning vector (Clontech; catalog #HL 1067 J) was screened for the 5' end of the gene coding for L5/3 with a mouse genomic fragment containing the first exon of the gene for mouse L5/3. This fragment was 400 bp in length and was isolated by digestion of a genomic subclone from the mouse gene (a 3.3 kb Bgl II fragment cloned into the Bam HI site of pBR322) with Bam HI and Eco RI (nucleotides 1086–1486 in Sequence ID No. 5). Approximately, 500,000 recombinant phage were screened under identical reduced stringency conditions discussed above for the original isolation of the L5 gene. Thirteen positives were identified; three were characterized and found to code for the 5' end of the human L5/3 gene (referred to as L3).

Fragments from two overlapping phage (L5 and L3) were subcloned into pBR322 and the DNA sequence of the inserts were determined. The entire sequence of the gene present in L5 and L3 is shown in Sequence ID No. 6. This gene is the complete gene L5/3 of the present invention. The gene is 4690 bp in length (from the codon for the putative initiator methionine to the polyadenylation site; nucleotides 274–4963 in Sequence ID No. 6). The gene is composed of 18 exons separated by 17 intervening sequences. In addition, sequence has been determined both upstream and downstream of the gene.

The 3' end of the acyl-peptide hydrolase gene is 444 base pairs downstream of L5/3 gene on the complementary strand (nucleotides 5408 to 6100 in Sequence ID No. 6).

Several isolated cDNA fragments were characterized. One cDNA (#19) had two parts of the coding region deleted when compared to cDNA (#33) which included nucleotides 1366–1486 and 1565–1613 in Sequence ID No. 1. The cDNA for #19 is Sequence ID No. 3. In the L5/3 gene the region deleted included exon 13 (nucleotides 3532–3652 in Sequence ID No. 6) and the 5' end of exon 18 (nucleotides 4033–4081 in Sequence ID No. 6). If this cDNA represents a translated mRNA, it would code for the four kringle domains followed by only 22 amino acids since there are two in-frame stop codons at that point.

Comparison of all cDNA sequences indicates that at least five polymorphisms occur; only one of which results in an amino acid substitution. This substitution is a Cys (Sequence ID No. 1) to Phe (Sequence ID No. 2) at amino acid residue 212. When the sequence of the exons in the L5/3 gene are compared to the cDNA sequences, one additional polymorphic site is identified that results in a Tyr (in the cDNAs; Sequence ID No.1 and Sequence ID No. 2) to Cys (in the gene; Sequence ID No. 6) substitution at residue 13. All of these polymorphisms should occur in the population and all would represent functional L5/3 protein.

The gene and cDNA coding for L5/3 codes for a protein with similar domain structure as HGF with four kringles followed by a serine protease-like domain. The translated amino acid sequences of the gene (shown in the FIGURE) and cDNA for human L5/3 predict a protein with 80,325 molecular weight containing 711 amino acids (excluding additional post-translational processing). The FIGURE is a schematic diagram of the amino acid sequence of human L5/3. The amino acid sequence of human L5/3 is shown starting with residue 1 at the amino-terminal end and ending with residue 711 at the carboxy-terminal end. Placement of disulfide bonds was determined solely on the basis of homology with this protein sequence to plasminogen, where placement of disulfides has been determined. The four kringle domains are indicated by K1, K2, K3, and K4. The region homologous to the preactivation peptide of plasminogen is indicated by PAP. The three potential N-linked cleavage sites are indicated by open arrows. The sequence following the second open arrow is homologous to other serine proteases. The active site amino acids His, Asp and Ser have been changed to Gln, Gln and Tyr, respectively and are indicated in boxes. Amino acids are represented in the one letter code where A=Ala, C=Cys, D=Asp, E=Glu, F=Phe, G=Gly, H=His, I=Ile, K=Lys, L=Leu, M=Met, N=Asn, P=Pro, Q=Gln, R=Arg, S=Ser, T=Thr, V=Val, W=Trp and Y=Tyr. There are three potential carbohydrate additions sites at asparagines in the sequence Asn-X-Thr/Ser at positions 72, 296 and 615 (in the FIGURE). The sequence at the amino-terminal end of the putative protein is hydrophobic and therefore may be part of a signal sequence required for secretion of the protein from the cell. Comparison of the amino-terminal sequence to a consensus sequence compiled for known signal peptidase cleavage sites (Von Heijne, 1983; Watson, 1984) predicts that the cleavage site could be between residues Gly-31 and Thr-32 (in the FIGURE). The active protein coded by the L5/3 gene refers to the protein as modified during expression and passage through the cell wall. Thus the active protein would exclude the signal sequence which may include residues 1–31.

Based on homology to plasminogen and other serine proteases, two additional proteolytic cleavage sites are predicted. Between the kringle domain region and the serine protease-like domain is an amino acid sequence that is typically found at the activation sites of other coagulation and fibrinolytic proteins with serine protease activity. Residue 483 is an Arg followed by the sequence Val-Val-Gly-Gly that is typically found at the amino-terminal end of serine proteases (in the FIGURE). On the basis of this sequence, it is anticipated that active L5/3 protein is proteolytically cleaved to yield a two-chain molecule held together by disulfide bonds or cleaved into two separate polypeptide chains. Amino acid residues 56–103 in human L5/3 are homologous to the preactivation peptide (PAP) in plasminogen and HGF (in the FIGURE). The PAP region in plasminogen is between the amino-terminal end of the mature protein and the plasmin activation site between Lys-77 and Lys-78. Both lysines are conserved in L5/3 (residues 103 and 104 in the FIGURE). Cleavage at this site would remove a peptide of 103 amino acids from the protein (including the putative signal peptide) if it is not disulfide-bonded to the remainder of the protein (there is one additional cysteine in this region).

The amino acids found in the active site of serine proteases have been changed from His to Gln, Asp to Gln, and Ser to Tyr at positions 522, 568, and 661, respectively (in the FIGURE). Therefore, we anticipate that this protein has no proteolytic activity.

Only a portion of the entire primary structure may be required for function. Also included within the definition the active proteins coded for by the L5/3 gene are fragments of the entire sequence which retain activity particularly those which result from post-translational processing such as glycosylation. It is further understood that minor modifications of primary amino acid sequence may result in proteins which have substantially equivalent or enhanced activity as compared to any particular illustrated sequence. These modifications may be deliberate, as through site-directed mutagenesis, or may be accidental, such as mutations of hosts which are L5/3 producing organisms. All of these modifications are included as long as the activity of the L5/3 protein is retained.

The complete mouse L5/3 DNA sequence and the amino acid coding regions of the gene are shown in Sequence I.D. No. 5. The mouse L5/3 gene is composed of 18 exons separated by 17 intervening sequences. The gene is 4613 bp in length from the site of initiation of transcription to the polyadenylation site. (Nucleotides 1192 to 5804 in Sequence ID No. 5.) The gene coding for acyl-peptide hydrolase is 410 base pairs downstream of the L5/3 gene, but is transcribed from the complementary strand (nucleotides 6215–6751 in Sequence ID No. 5).

The mouse cDNA (Sequence ID No. 4) codes for a putative protein with the same domain structure as its human homolog with four kringle domains followed by a serine protease-like domain. Translated sequence from the gene and cDNA coding for mouse L5/3 indicate that a protein of 716 amino acids with a molecular weight of 80,593 would be synthesized (excluding any additional post-translational processing). There are four potential N-linked carbohydrate attachment sites at asparagines in the sequence Asn-X-Thr/Ser at positions 72, 173, 305 and 624. The sequence at the amino-terminal end of the putative protein is hydrophobic and therefore may be part of a signal sequence required for secretion of the protein from the cell. Based on homology with the human cDNA the signal peptidase cleavage site is between amino acid residues Gly-31 and Thr-32 Sequence ID No. 4.

There is only one difference found when the sequences of the cDNA and gene coding for mouse L5/3 are compared which results in the substitution of a Gln in the gene (Sequence ID No. 5) to a Pro in the cDNA (Sequence ID No. 4) at residue 19. It is anticipated that this site is polymorphic in the population and that both are representatives of functional L5/3 protein.

The primary site of synthesis of mRNA for L5/3 is in the liver as determined by analysis of rat tissue RNA by Northern analysis. Lesser amounts of L5/3 mRNA were found in the lung, adrenal, and placenta.

A fusion protein was produced as well as polyclonal antibodies. A 968 bp fragment from the human L5/3 cDNA (#33) was obtained after digestion with Bam HI and Bgl II and cloned into the prokaryotic expression vector pUR278 (Ruther & Muller-Hill, 1983). This fragment represents nucleotides 746–1714 in Sequence ID No. 1 and codes for part of kringle 2, all of kringles 3 and 4 and part of the serine protease-like domain of L5/3. In pUR278, the L5/3 cDNA fragment was cloned into the Bam HI site near the 3' end of the lac Z gene to allow for expression of an active β-galactosidase fused with the peptide encoded by the L5/3 cDNA fragment in E. coli. The correct reading frame was maintained in the construct as determined by DNA sequence analysis. The 968 bp insert codes for 321 amino acids (residues 255–576 in Sequence ID No. 1) with a calculated molecular weight of approximately 35,000 daltons. The predicted size for the fusion protein is approximately 151,000 daltons which contains the human L5/3 protein peptide fused to β-galactosidase (116,000 MW).

The fusion protein was isolated and electroeluted after SDS-polyacrylamide gel electrophoresis of isopropyl thiogalactoside (IPTG) induced E.coli cell extract from cells that had been transformed with the fusion construct.

Fusion protein (β-galactosidase/L5/3) was injected into New Zealand rabbits in order to obtain polyclonal antibodies against the fusion protein by standard techniques.

Tissue lysate from human liver and human plasma were electrophoresed on SDS-polyacrylamide gels under reducing condition, transferred to an Immobilon-P membrane (Amersham, Inc.) and reacted with rabbit anti-β-galactosidase/human L5/3 fusion protein serum. The antibody reacted primarily with a polypeptide of approximately 84,000 molecular weight in plasma and to a lesser extent with a polypeptide of 60,000 molecular weight. Non-immune serum did not react with polypeptides of these sizes on either reducing or non-reducing gels. The antibody did not react with any detectable protein in the liver extract. The antibody did not cross react with purified human prothrombin. On non-reducing gels the antibody detected a protein of approximately 90,000 molecular weight.

These results are consistent with the presence of a signal peptide at the amino-terminal of L5/3 that is required for secretion from the cell since the antibody reacted only with a polypeptide present in plasma and not in liver extract. The signal peptide of approximately 3500 daltons would be removed before secretion from the cell. In addition, these results are consistent with proteolysis at possibly both of the putative proteolytic sites present in L5/3 (in the FIGURE). Based on the translated cDNA sequence, the full-length protein would be approximately 80,000 daltons. Carbohydrate addition to some or all of the three possible N-linked glycosylation sites might increase the molecular weight to the approximately 90,000 dalton size seen in plasma on non-reducing gels. On reducing gels where the disulfide bonds have been removed, the 84,000 molecular weight protein could be the result of proteolytic cleavage between amino acid residues 103 and 104 (Sequence ID No. 1 in the FIGURE). The predicted size of the protein with the amino-terminal 103 residues removed is approximately 70,000 daltons. The 84,000 molecular weight protein may be this fragment of L5/3 after glycosylation. On non-reducing gels this fragment could possibly be disulfide-bonded to the remainder of the protein (there is one additional cysteine in this part of the protein that could be involved in disulfide formation) and may be the reason why a larger protein was observed on the non-reduced gel compared tO the reduced one. The 60,000 dalton polypeptide also seen in plasma on reducing gels could be the result of additional proteolytic cleavage of the protein between residues 483 and 484 (Sequence ID No. 1 in the FIGURE) which is a typical serine protease activation site. The resultant fragments would have molecular weights of 50,000 and 25,000 daltons (excluding any post-translational modifications such as glycosylation). If the two potential N-linked carbohydrate addition sites in the 50,000 dalton fragment are glycosylated the fragment could be 60,000 daltons in size. The smaller fragment may not have been resolved on this gel or the antibody may not react with it.

These results are analogous to the form of HGF seen in plasma which is a heterodimeric protein of 82,000 daltons composed of α and β subunits of 51,000 and 26,000 daltons, respectively.

A full-length human L5/3 cDNA was then constructed. Since the longest human L5/3 cDNA was not full-length and was missing 16 bp from the 5' end (Sequence ID No. 1), a full-length L5/3 cDNA was constructed by addition of adaptors. The following complementary oligonucleotides were synthesized: coding: 5' GCGAATTCCACC ATGGGGTGGCTCCCA 3' (SEQ ID NO:9) complementary 3' CGCTTAAGGTGGTACCCCACCGAGGGTTTAA 5' (SEQ ID NO:10).

When hybridized to each other this adaptor has the following features: 1) the presence of an Eco RI restriction site (5' GAATTC 3') at the 5' end for cloning into the Eco RI sites in expression vectors; 2) a Kozak consensus sequence surrounding the ATG coding for the initiator methionine (5' CCACCATGG 3'; Kozak, 1986) to optimize translation from this methionine; 3) an overhanging-end at the 3' end of the adaptor that is compatible with the EcoRI site present at the 5' end of the L5/3cDNA-(33) for ligation together; and 4) after ligation of the adaptor to the cDNA insert the Eco RI sites at the ends of the original cDNA will not be reconstituted and therefore the only Eco RI sites will be due to the adaptor.

The 2200 bp cDNA insert from the human L5/3cDNA-(33) was isolated after digestion with Eco RI (nucleotides 1–2219 in Sequence ID No. 1) and ligated to the hybridized oligonucleotides (adaptor). The resulting mixture was digested with Eco RI and electrophoresed on low melting point agarose. The band representing the cDNA with ligated adaptors was excised and the DNA isolated. This DNA was then ligated to the vector Bluescript SK± (Stratagene, La Jolla, Calif.), and used to transform *E. coli*. *E. Coli* transformed with the anticipated full-length L5/3cDNA containing plasmid were initially identified by restriction enzyme digestion of plasmid isolated from white colonies on agar plates containing IPTG, X-Gal and ampicillin (*E. coli* containing the recombinant vector will give white colonies while Bluescript without an insert will give blue colonies). Final confirmation of the full-length construct was determined by DNA sequence analysis.

After adaptor ligation to the human L5/3 cDNA insert there are eight nucleotide differences when the sequence is compared to the exons in the gene for human L5/3 (nucleotides 1301–1312 in Sequence ID No. 6). These are due to the original Eco RI site present at the 5' end of the L5/3cDNA insert that is the result of linker addition during the construction of the cDNA library and is not naturally present in the cDNA (as determined from the sequence of the gene for this region). These differences result in three amino acid substitutions that we do not anticipate will affect the function of recombinant full-length L5/3 protein since they are present in the proposed signal peptide. The sequence of the full-length construct is shown in Sequence ID No. 7. Residues 6–8 are Leu-Leu-Leu in the gene coding for human L5/3 (Sequence ID No. 6) and Asn-Ser-Val in the full length L5/3 cDNA (Sequence ID No. 7). Adaptor(s) are also present at the 3' end of the cDNA but should not affect the expression of L5/3 since they are present in the 3' noncoding region of the cDNA.

Mammalian expression vectors were also constructed. The full-length L5/3 insert was isolated from the Bluescript vector after digestion with Eco RI. The insert was then cloned into the Eco RI site of the expression vector pDX. This expression vector was obtained from Dr. Kathy Berkner of Zymogenetics. pDX contains an origin of replication, a SV-40 enhancer, a adenovirus promoter, splice sequences and a polyadenylation signal for appropriate replication and transcription of the inserted cDNA and the accurate synthesis and secretion of the expressed protein. The cDNA provides the signal sequence for secretion. This expression vector has been used to transfect the eukaryotic cell line—Hela which does not normally express L5/3 protein.

Expression in general may be achieved in a variety of host systems including, in particular, mammalian and bacterial systems, as well as yeast based systems. In addition, other cell systems have become available such as the baculovirus vectors used to express protein encoding genes in insect cells. The expression system discussed here is illustrative, and it is understood by those in the art that a variety of expression systems can be used.

Additional factors necessary or helpful in effecting expression may subsequently be identified.

As the nucleotide sequences encoding the human and mouse L5/3 proteins are now available, these may be expressed in a variety of systems. If procaryotic systems are used, an intronless coding sequence should be used, along with suitable control sequences. The cDNA clones for any of the above L5/3 proteins may be excised with suitable restriction enzymes and ligated into procaryotic vectors for such expression. For procaryotic expression of L5/3 genomic DNA, the DNA should be modified to remove the introns, either by sitedirected mutagenesis, or by retrieving corresponding portions of cDNA and substituting them for the intron-containing genomic sequences. The intronless coding DNA is then ligated into expression vectors for procaryotic expression.

As discussed above, L5/3 encoding sequences may also be used directly in an expression system capable of processing the introns, usually a mammalian host cell culture. To effect such expression, the genomic sequences can be ligated downstream from a controllable mammalian promoter which regulates the expression of these sequences in suitable mammalian cells.

E. coli RRI cells carrying the plasmid containing LS/3cDNA (#33) exhibited in Sequence ID No. 1 has been deposited with the American Type Cell Culture in Rockville, Md. and is designated ATCC No. 68976 (deposited on May 6, 1992).

The gene sequence No. 1 submitted below is useful of course when labeled by for example Nick translation as a probe for the D3F15S2 locus on human chromosome 3. This is significant with respect to detection of mutations which provide an indication of one's predisposition to lung carcinoma, renal cell carcinoma and Von Hipple-Lindau syndrome. Further, the protein coded by the DNA and associated cDNA is useful as an in vitro growth promoter particularly for hepatocytes. This can be used to alter growth characteristics of hepatocytes by combining minor amounts (0.1 to 100 nanograms) of the protein per milliliter of growth serum with hepatocytes.

Further the antibody to the L5/3 protein is useful for detection of the L5/3 protein in human serum. This again is useful for the purpose of again detecting any alteration of the chromosome 3 locus D3F15S2 and again an indication of the predisposition towards cancer.

Further, cited below are the DNA sequences for both the human and the mouse along with the cDNA sequences for the human and mouse and the protein associated with the human DNA.

Sequence ID No. 1: cDNA for Human L5/3 clone #33 and associated protein.

Sequence ID No. 2: cDNA for Human L5/3 clone #33 with polymorphism relative to Sequence ID No. 1 and associated protein.

Sequence ID No. 3: cDNA for Human L5/3 clone #19 and associated protein.

Sequence ID No. 4: cDNA for Mouse L5/3 and associated protein.

Sequence ID No. 5: DNA for Mouse L5/3 and associated protein.

Sequence ID No. 6: DNA Sequence of Human L5/3 and associated protein.

Sequence ID No. 7: cDNA Sequence of Human L5/3 with 5' and 3' adaptors added to make a full length cDNA.

Sequence ID No. 8: DNA Sequence human L5/3 depicted in the FIGURE.

I claim:

1. The recombinant protein coded for by the DNA sequence located at D3F15S2 locus on human chromosome 3 having 18 exons coding for a human growth factor, said human growth factor comprising an approximately 80,000 dalton, single-chain protein containing four Kringle Domains.

2. The recombinant protein claimed in claim 1 having the amino acid sequence coded for by the cDNA of SEQ ID NO:1.

3. The recombinant protein claimed in claim 1 having the amino acid sequence coded for by the cDNA of SEQ ID NO:2.

4. The protein depicted in FIG. 1 and having the amino acid sequence of SEQ ID NO:8.

5. The recombinant protein claimed in claim 1 having the amino acid sequence coded for by the cDNA of SEQ ID NO:7.

* * * * *